(12) United States Patent
Gee et al.

(10) Patent No.: US 12,119,119 B2
(45) Date of Patent: Oct. 15, 2024

(54) METHODS AND SYSTEMS FOR REAL-TIME SENSOR MEASUREMENT SIMULATION

(71) Applicant: MEDTRONIC MINIMED, INC., Northridge, CA (US)

(72) Inventors: Elaine Gee, Windsor, CA (US); Peter Ajemba, Canyon Country, CA (US); Bahman Engheta, Santa Monica, CA (US); Jeffrey Nishida, Chicago, IL (US); Andrea Varsavsky, Santa Monica, CA (US); Keith Nogueira, Mission Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 338 days.

(21) Appl. No.: 16/848,695

(22) Filed: Apr. 14, 2020

(65) Prior Publication Data
US 2021/0170103 A1 Jun. 10, 2021

Related U.S. Application Data

(60) Provisional application No. 62/945,800, filed on Dec. 9, 2019.

(51) Int. Cl.
*G16H 50/00* (2018.01)
*A61B 5/00* (2006.01)
(Continued)

(52) U.S. Cl.
CPC .......... *G16H 50/50* (2018.01); *A61B 5/0022* (2013.01); *A61B 5/1451* (2013.01);
(Continued)

(58) Field of Classification Search
CPC ........ G16H 40/40; G16H 40/67; G16H 20/17; G16H 20/70; G16H 20/30; G16H 70/60;
(Continued)

(56) References Cited

U.S. PATENT DOCUMENTS

| 4,562,751 A | 1/1986 | Nason et al. |
| 4,685,903 A | 8/1987 | Cable et al. |

(Continued)

OTHER PUBLICATIONS

Stephanie L. Hyland, et al., Real-Valued (Medical) Time Series Generation with Recurrent Conditional GANs, Tri-Institutional Training Program in Computational Biology and Medicine, Weill Cornell Medical, Dec. 4, 2017.

(Continued)

*Primary Examiner* — Nathan R Price
*Assistant Examiner* — Tania Ismail
(74) *Attorney, Agent, or Firm* — Weaver Austin Villeneuve & Sampson LLP

(57) ABSTRACT

Medical devices and related systems and methods are provided. A method of estimating a physiological condition using a first sensing arrangement involves obtaining a sensor translation model associated with a relationship between the first sensing arrangement and a second sensing arrangement, wherein the second sensing arrangement is different from the first sensing arrangement, obtaining one or more measurements from a sensing element coupled to the processing system of the first sensing arrangement, determining simulated measurement data for the second sensing arrangement by applying the sensor translation model to the one or more measurements from the sensing element of the first sensing arrangement, and determining an estimated value for the physiological condition by applying an estimation model associated with the second sensing arrangement to the simulated measurement data.

21 Claims, 7 Drawing Sheets

(51) Int. Cl.

| | | |
|---|---|---|
| *A61B 5/145* | (2006.01) | |
| *G06F 18/214* | (2023.01) | |
| *G06N 3/045* | (2023.01) | |
| *G06N 3/0475* | (2023.01) | |
| *G06N 3/088* | (2023.01) | |
| *G16H 10/60* | (2018.01) | |
| *G16H 20/17* | (2018.01) | |
| *G16H 40/40* | (2018.01) | |
| *G16H 40/67* | (2018.01) | |
| *G16H 50/20* | (2018.01) | |
| *G16H 50/30* | (2018.01) | |
| *G16H 50/50* | (2018.01) | |
| *G16H 50/70* | (2018.01) | |
| *G16H 70/60* | (2018.01) | |
| *A61B 5/1495* | (2006.01) | |
| *A61M 5/172* | (2006.01) | |

(52) U.S. Cl.
CPC ........ *A61B 5/14532* (2013.01); *A61B 5/7253* (2013.01); *A61B 5/7267* (2013.01); *A61B 5/7275* (2013.01); *G06F 18/214* (2023.01); *G06N 3/045* (2023.01); *G06N 3/0475* (2023.01); *G06N 3/088* (2013.01); *G16H 10/60* (2018.01); *G16H 20/17* (2018.01); *G16H 40/40* (2018.01); *G16H 40/67* (2018.01); *G16H 50/20* (2018.01); *G16H 50/30* (2018.01); *G16H 50/70* (2018.01); *G16H 70/60* (2018.01); *A61B 5/1495* (2013.01); *A61B 2560/0223* (2013.01); *A61B 2560/0228* (2013.01); *A61M 5/1723* (2013.01); *A61M 2205/3303* (2013.01); *A61M 2205/50* (2013.01); *A61M 2205/52* (2013.01); *A61M 2205/70* (2013.01); *A61M 2230/201* (2013.01)

(58) Field of Classification Search
CPC ........ G16H 50/50; G16H 50/20; G16H 50/70; G16H 10/60; A61B 5/0022; A61B 5/1451; A61B 5/14532; A61B 5/4267; A61B 5/7275; A61B 5/1495; A61B 2560/0223; A61B 2560/0228; A61B 2562/028; A61B 2562/085; A61M 5/1723; A61M 2205/3303; A61M 2205/50; A61M 2205/52; A61M 2205/70; A61M 2230/201

See application file for complete search history.

(56) References Cited

U.S. PATENT DOCUMENTS

| | | | |
|---|---|---|---|
| 4,755,173 | A | 7/1988 | Konopka et al. |
| 5,080,653 | A | 1/1992 | Voss et al. |
| 5,097,122 | A | 3/1992 | Colman et al. |
| 5,391,250 | A | 2/1995 | Cheney, II et al. |
| 5,485,408 | A | 1/1996 | Blomquist |
| 5,505,709 | A | 4/1996 | Funderburk et al. |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,088,608 | A | 7/2000 | Schulman et al. |
| 6,119,028 | A | 9/2000 | Schulman et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,485,465 | B2 | 11/2002 | Moberg et al. |
| 6,544,212 | B2 | 4/2003 | Galley et al. |
| 6,554,798 | B1 | 4/2003 | Mann et al. |
| 6,558,320 | B1 | 5/2003 | Causey, III et al. |
| 6,558,351 | B1 | 5/2003 | Steil et al. |
| 6,589,229 | B1 | 7/2003 | Connelly et al. |
| 6,591,876 | B2 | 7/2003 | Safabash |
| 6,641,533 | B2 | 11/2003 | Causey, III et al. |
| 6,659,980 | B2 | 12/2003 | Moberg et al. |
| 6,736,797 | B1 | 5/2004 | Larsen et al. |
| 6,740,072 | B2 | 5/2004 | Starkweather et al. |
| 6,749,587 | B2 | 6/2004 | Flaherty |
| 6,752,787 | B1 | 6/2004 | Causey, III et al. |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 6,817,990 | B2 | 11/2004 | Yap et al. |
| 6,827,702 | B2 | 12/2004 | Lebel et al. |
| 6,932,584 | B2 | 8/2005 | Gray et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,323,142 | B2 | 1/2008 | Pendo et al. |
| 7,399,277 | B2 | 7/2008 | Saidara et al. |
| 7,402,153 | B2 | 7/2008 | Steil et al. |
| 7,442,186 | B2 | 10/2008 | Blomquist |
| 7,602,310 | B2 | 10/2009 | Mann et al. |
| 7,621,893 | B2 | 11/2009 | Moberg et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 8,474,332 | B2 | 7/2013 | Bente, IV |
| 8,674,288 | B2 | 3/2014 | Hanson et al. |

(56) References Cited

U.S. PATENT DOCUMENTS

| | | | |
|---|---|---|---|
| 10,282,588 | B2 | 5/2019 | Comaniciu et al. |
| 11,272,869 | B2 | 3/2022 | Kamath et al. |
| 11,517,223 | B2 | 12/2022 | Choi et al. |
| 11,670,425 | B2 | 6/2023 | Gee et al. |
| 2006/0031094 | A1 | 2/2006 | Cohen et al. |
| 2007/0123819 | A1 | 5/2007 | Vernoe et al. |
| 2009/0192366 | A1 | 7/2009 | Mensinger et al. |
| 2010/0160861 | A1 | 6/2010 | Causey, III et al. |
| 2013/0338630 | A1 | 12/2013 | Agrawal et al. |
| 2014/0066889 | A1 | 3/2014 | Grosman et al. |
| 2018/0169334 | A1 | 6/2018 | Grosman et al. |
| 2018/0272063 | A1* | 9/2018 | Neemuchwala ....... G16H 20/17 |
| 2019/0076066 | A1 | 3/2019 | Ajemba et al. |
| 2021/0174949 | A1 | 6/2021 | Gee et al. |
| 2021/0174960 | A1 | 6/2021 | Gee et al. |
| 2022/0104735 | A1 | 4/2022 | Lee et al. |
| 2023/0000402 | A1 | 1/2023 | Ajemba et al. |
| 2023/0260664 | A1 | 8/2023 | Gee et al. |
| 2023/0352186 | A1 | 11/2023 | Gee et al. |

OTHER PUBLICATIONS

Ian J. Goodfellow, et al., Generative Adversarial Nets, Computer Science and Operations Research Department, University of Montreal, Montreal, QC, Canada, Jun. 10, 2014.

Zeyu Jin, et al., Cute: a Concatenative Method for Voice Conversion Using Exemplar-Based Unit Selection, Princeton University, Princeton, NJ & Adobe Research, San Francisco, CA.

Skyler Norgaard, et al., Synthetic Sensor Data Generation for Health Applications: a Supervised Deep Learning Approach, Department of Computer Science, Kalamazoo College, Kalamazoo, MI & School of Electrical Engineering and Computer Science, Washington State University, Pullman, WA.

Aaron Van Den Oord, et al., WaveNet: a Generative Model for Raw Audio, Google DeepMind, London, UK, pp. 1-15.

Jeremy Jordan, Variational Autoencoders, Mar. 19, 2018, Retrieved from the Internet on Oct. 11, 2019 from: https://www.jeremyjordan.me/variational-autoencoders/.

Felipe Petroski Such, et al., Generative Teaching Networks: Accelerating Neural Architecture Search by Learning to Generate Synthetic Training Data, Dec. 18, 2019, Retrieved from the Internet from: https://eng.uber.com/generative-teaching-networks/.

Jonathan Tremblay, et al., Training Deep Networks with Synthetic Data: Bridging the Reality Gap by Domain Randomization, Apr. 18, 2018, Retrieved from https://arxiv.org/abs/1804.06516.

U.S. Notice of Allowance dated Nov. 9, 2022 in U.S. Appl. No. 16/848,687.

U.S. Non-Final office Action dated Apr. 28, 2022 in U.S. Appl. No. 16/848,687.

U.S. Non-Final Office Action dated Apr. 6, 2023 in U.S. Appl. No. 16/848,710.

U.S. Notice of Allowance dated May 4, 2023 in U.S. Appl. No. 16/848,687.

U.S. Notice of Allowance dated Jan. 25, 2023 in U.S. Appl. No. 16/848,687.

* cited by examiner

METHODS AND SYSTEMS FOR REAL-TIME SENSOR MEASUREMENT SIMULATION

CROSS-REFERENCE TO RELATED APPLICATION(S)

This application claims the benefit of U.S. Provisional Patent Application Ser. No. 62/945,800, filed Dec. 9, 2019, the contents of which are incorporated by reference herein in its entirety.

TECHNICAL FIELD

Embodiments of the subject matter described herein relate generally to medical devices, and more particularly, embodiments of the subject matter relate to calibrating sensing devices for use with medical devices, such as fluid infusion devices.

BACKGROUND

Infusion pump devices and systems are relatively well known in the medical arts, for use in delivering or dispensing an agent, such as insulin or another prescribed medication, to a patient. Control schemes have been developed to allow insulin infusion pumps to monitor and regulate a patient's blood glucose level in a substantially continuous and autonomous manner. Rather than continuously sampling and monitoring a user's blood glucose level, which may compromise battery life, intermittently sensed glucose data samples are often utilized for purposes of continuous glucose monitoring (CGM) or determining operating commands for the infusion pump.

Many continuous glucose monitoring (CGM) sensors measure the glucose in the interstitial fluid (ISF). Typically, to achieve the desired level of accuracy and reliability and reduce the impact of noise and other spurious signals, the sensor data is calibrated using a known good blood glucose value, often obtained via a so-called "fingerstick measurement" using blood glucose meters that measures the blood glucose in the capillaries. However, performing such calibration measurements increases the patient burden and perceived complexity, and can be inconvenient, uncomfortable, or otherwise disfavored by patients. Moreover, ISF glucose measurements lag behind the blood glucose measurements based on the time it takes glucose to diffuse from the capillary to the interstitial space where it is measured by the CGM sensor, which requires signal processing (e.g., filtering) or other techniques to compensate for physiological lag. Additionally, various factors can lead to transient changes in the sensor output, which may influence the accuracy of the calibration. Degradation of sensor performance over time or manufacturing variations may further compound these problems.

To decrease the patient burden associated with obtaining reference measurements and improve the user experience, machine learning or artificial intelligence techniques have been utilized to develop models for generating calibrated measurements. However, to avoid compromising accuracy or reliability, these approaches often require relatively large data sets to achieve the desired model performance. Obtaining large data sets often entails increased time and costs associated with data collection, which is a significant clinical burden when utilizing such modeling techniques in newly developed sensing devices that is a challenge to condensed development cycles or relatively limited clinical trials (e.g., a limited number of patients and/or a limited trial duration). Accordingly, it is desirable to provide support for model-based calibration in situations where limited data is available.

BRIEF SUMMARY

Medical devices and related systems and operating methods are provided for generating simulated measurement data. The simulated measurement data may be utilized to develop glucose estimation models or other predictive models for a physiological condition based on measurement signals output by a given sensing arrangement. One exemplary method of estimating a physiological condition using a first sensing arrangement influenced by the physiological condition involves determining, by a computing device, a translation model based at least in part on relationships between first measurement data corresponding to instances of the first sensing arrangement and second measurement data corresponding to instances of a second sensing arrangement, wherein the second sensing arrangement is different from the first sensing arrangement, obtaining, by the computing device, third measurement data associated with the second sensing arrangement, determining, by the computing device, simulated measurement data for the first sensing arrangement by applying the translation model to the third measurement data, and determining, by the computing device, an estimation model for the physiological condition using the simulated measurement data, wherein the estimation model is applied to subsequent measurement output provided by an instance of the first sensing arrangement to obtain an estimated value for the physiological condition.

In another embodiment, a method of estimating a glucose level using a first glucose sensing arrangement involves obtaining a translation model for output of the first glucose sensing arrangement, the translation model being based at least in part on relationships between first sensor measurement data obtained from instances of the first glucose sensing arrangement and second sensor measurement data corresponding to instances of a second glucose sensing arrangement, the second glucose sensing arrangement having a type or configuration different from the first glucose sensing arrangement, obtaining historical sensor measurement data associated with the second glucose sensing arrangement, obtaining historical reference measurement data corresponding to the historical sensor measurement data, determining simulated sensor measurement data for the first glucose sensing arrangement by applying the translation model to the historical sensor measurement data, deriving a glucose estimation model for the first glucose sensing arrangement using the simulated sensor measurement data and the historical reference measurement data, and thereafter inputting measurement outputs from an instance of the first glucose sensing arrangement to the glucose estimation model to obtain an estimated sensor glucose measurement value.

In another embodiment, a system is provided that includes a database to store first sensor measurement data corresponding to instances of a first sensing arrangement influenced by a physiological condition and second sensor measurement data corresponding to instances of a second sensing arrangement influenced by the physiological condition, wherein a type or configuration of the second sensing arrangement is different from the first sensing arrangement, and a server coupled to the database and a network to determine a translation model associated with the first sensing arrangement based at least in part on relationships between the first sensor measurement data and a first subset of the second sensor measurement data, determine simulated measurement data for the first sensing arrangement by applying the translation model to a second subset of the second sensor measurement data, determine an estimation model for the physiological condition using the simulated measurement data, and provide the estimation model associated with the first sensing arrangement to a computing device via the network.

In another exemplary embodiment, a method of estimating a physiological condition using a first sensing arrangement is provided. The method involves obtaining, by a processing system of the first sensing arrangement, a sensor translation model associated with a relationship between the first sensing arrangement and a second sensing arrangement, wherein the second sensing arrangement is different from the first sensing arrangement, obtaining, by the processing system, one or more measurements from a sensing element coupled to the processing system of the first sensing arrangement, determining, by the processing system, simulated measurement data for the second sensing arrangement by applying the sensor translation model to the one or more measurements from the sensing element of the first sensing arrangement, and determining, by the processing system, an estimated value for the physiological condition by applying an estimation model for the physiological condition associated with the second sensing arrangement to the simulated measurement data.

In another embodiment, a method of estimating a glucose level using a first glucose sensing arrangement involves obtaining a translation model for output of the first glucose sensing arrangement, the translation model being based at least in part on relationships between first sensor measurement data obtained from instances of the first glucose sensing arrangement and second sensor measurement data corresponding to instances of a second glucose sensing arrangement, the second glucose sensing arrangement having a type or configuration different from the first glucose sensing arrangement, obtaining one or more measurements from a sensing element coupled to a processing system of the first glucose sensing arrangement, determining simulated measurement data in a measurement domain associated with the second glucose sensing arrangement by applying the translation model to the one or more measurements, and determining an estimated value for the glucose level by applying a sensor glucose estimation model associated with the second glucose sensing arrangement to the simulated measurement data.

In another embodiment, an apparatus for a glucose sensor is provided. The glucose sensor includes a data storage element to maintain a sensor translation model associated with a relationship with a different glucose sensor and a glucose estimation model associated with the different glucose sensor, an output interface, a glucose sensing element to obtain one or more measurements influenced by a glucose level of a patient, and a processing system coupled to the glucose sensing element and the data storage element to determine simulated measurement data by applying the sensor translation model to the one or more measurements, determine an estimated value for the glucose level of the patient by applying the glucose estimation model to the simulated measurement data, and provide the estimated value to the output interface.

In another exemplary embodiment, a method of estimating a physiological condition using a first sensing arrangement influenced by the physiological condition involves obtaining, by a computing device, reference measurement data for the physiological condition, obtaining, by the computing device, first measurement data corresponding to the reference measurement data from one or more instances of the first sensing arrangement, determining, by the computing device, a generative model associated with the first sensing arrangement based on relationships between the first measurement data and the reference measurement data, obtaining, by the computing device, second reference measurement data for the physiological condition, generating, by the computing device, simulated measurement data corresponding to the second reference measurement data by applying the generative model to the second reference measurement data, and determining, by the computing device, an estimation model for the physiological condition based at least in part on relationships between the simulated measurement data and the second reference measurement data, wherein the estimation model is applied to subsequent measurement output provided by an instance of the first sensing arrangement to obtain an estimated value for the physiological condition.

In another embodiment, a method of estimating a glucose level using a glucose sensing arrangement involves obtaining a generative model associated with the glucose sensing arrangement, obtaining reference glucose measurement data from one or more instances of a blood glucose meter, applying the generative model to the reference glucose measurement data to obtain simulated measurement data for the glucose sensing arrangement, determining an estimation model for the glucose sensing arrangement based at least in part on relationships between the simulated measurement data and the reference glucose measurement data, and applying the estimation model to one or more output measurements from a sensing element of the glucose sensing arrangement to obtain an estimated value for the glucose level using the glucose sensing arrangement.

In another embodiment, a system is provided that includes a database to store historical calibration data corresponding to instances of a first sensing arrangement, the historical calibration data comprising respective sets of a reference measurement value, a calibration factor value, and a timestamp value, and a server coupled to the database and a network to obtain the historical calibration data from the database, determine a generative model based on relationships between measurement data obtained from a second sensing arrangement and temporally associated calibration data, apply the generative model associated with the second sensing arrangement to the historical calibration data to obtain respective sets of simulated measurement data for the second sensing arrangement as a function of the respective sets of the calibration factor value and the timestamp value, determine an estimation model for the second sensing arrangement based at least in part on relationships between the respective sets of simulated measurement data and the corresponding respective reference measurement values, and provide the estimation model associated with the second sensing arrangement to a computing device via the network, wherein the computing device applies the estimation model to one or more output measurements from a sensing element of an instance of the second sensing arrangement to obtain an estimated calibrated measurement value.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
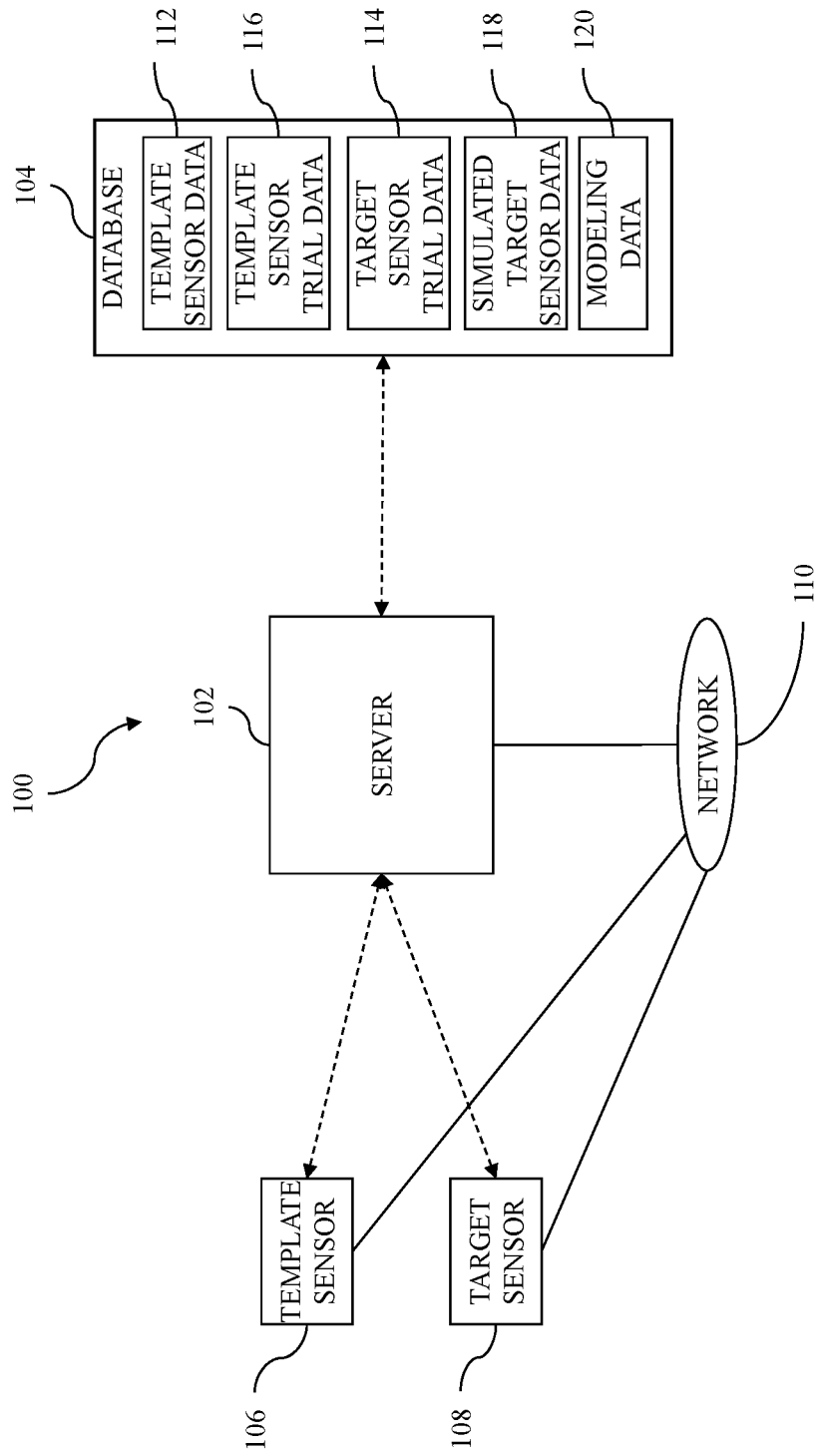
FIG. 1 depicts an exemplary embodiment of data management system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein generally relate to calibrating sensing elements and related sensing arrangements and devices that provide an output that is indicative of and/or influenced by one or more characteristics or conditions that are sensed, measured, detected, or otherwise quantified by the sensing element. While the subject matter described herein is not necessarily limited to any particular type of sensing application, exemplary embodiments are described herein primarily in the context of a sensing element that generates or otherwise provides electrical signals indicative of and/or influenced by a physiological condition in a body of a human user or patient, such as, for example, interstitial glucose sensing elements that provide electrochemical signals indicative of and/or influenced by a glucose level in an interstitial fluid compartment.

As described in greater detail below, observed measurement data obtained using different instances of a sensing arrangement or sensing element is utilized to characterize the electrochemical behavior of the particular sensing arrangement or sensing element and generate a corresponding model of the electrochemical response by the particular sensing arrangement or sensing element. The electrochemical response model is then utilized to generate simulated measurement data for different representative instances of the particular sensing arrangement or sensing element. The simulated measurement data is utilized, either individually or in combination with the observed measurement data, to generate a corresponding model for converting the electrical signals output by respective instances of the sensing arrangement or sensing element into an estimated calibrated measurement value. In this regard, by increasing the size of the data set being analyzed and modeled by including the simulated measurement data, the accuracy or other performance characteristics of the resultant model is improved. As described in greater detail below, in exemplary embodiments, a glucose estimation model for mapping one or more electrical signals output by an interstitial glucose sensing element into an estimated calibrated interstitial glucose measurement value is developed, derived, or otherwise determined using simulated measurement data, thereby improving the accuracy, reliability and/or other performance characteristics of the glucose estimation model to facilitate obtaining effectively calibrated measurement values for the glucose level of a patient in a manner that reduces reliance on so-called "fingerstick measurement" or other reference measurements.

It should be noted that the subject matter described herein is not necessarily limited to electrochemical signals, and in practice, could be implemented in an equivalent manner in the context of other types of sensors and other multi-dimensional and/or time-dependent signals (e.g., optical signals, electrical signals, or the like). Additionally, for purposes of explanation, exemplary embodiments of the subject matter are described herein as being implemented in conjunction with medical devices, such as portable electronic medical devices. Although many different applications are possible, the following description may focus on glucose sensing devices, continuous glucose monitoring (CGM) devices, or the like. That said, the subject matter may be implemented in an equivalent manner in the context of other medical devices, such as a fluid infusion device (or infusion pump) as part of an infusion system deployment, injection pens (e.g., smart injection pens), and the like. For the sake of brevity, conventional techniques related to glucose sensing, glucose monitoring, infusion system operation, insulin pump and/or infusion set operation, and other functional aspects of the systems (and the individual operating components of the systems) may not be described in detail here. It should be noted that the subject matter described herein can be utilized more generally in the context of overall diabetes management or other physiological conditions independent of or without the use of an infusion device or other medical device (e.g., when oral medication is utilized), and the subject matter described herein is not limited to any particular type of medication. In this regard, the subject matter is not limited to medical applications and could be implemented in any device or application that includes or incorporates a sensing element.

FIG. 1 depicts an exemplary embodiment of a data management system 100 suitable for implementing the subject matter described herein. The data management system 100 includes, without limitation, a computing device 102 coupled to a database 104, with the computing device 102 also being communicatively coupled to any number of additional electronic devices 106, 108 over a communications network 110, such as, for example, the Internet, a cellular network, a wide area network (WAN), or the like. It should be appreciated that FIG. 1 depicts a simplified representation of a data management system 100 for purposes of explanation and is not intended to limit the subject matter described herein in any way.

In exemplary embodiments described herein, the electronic devices 106, 108 are realized as sensing devices. That said, in other embodiments, the computing device 102 may support communications with other medical devices (e.g., an infusion device, a monitoring device, and/or the like) and/or any number of non-medical client electronic devices, such as, for example, a mobile phone, a smartphone, a tablet computer, a smart watch, or other similar mobile electronic device, or any sort of electronic device capable of communicating with the computing device 102 via the network 110, such as a laptop or notebook computer, a desktop computer, a computer cluster, or the like. In this regard, although FIG. 1 depicts the sensing devices 106, 108 communicating directly with the computing device 102 over the network 110, in alternative embodiments, the sensing devices 106, 108 may communicate indirectly with the computing device 102 via one or more intervening electronic devices (e.g., a patient's phone).

In one or more exemplary embodiments, sensing devices 106, 108 transmit, upload, or otherwise provide data or information to the computing device 102 for processing at the computing device 102 and/or for storage in the database 104. For example, as described in greater detail below, a sensing device 106, 108 may include a sensing element that is inserted into the body of a patient or otherwise worn by the patient to obtain measurement data indicative of a physiological condition in the body of the patient, with the sensing device 106, 108 periodically uploading or otherwise transmitting the measurement data to the computing device 102. In one or more embodiments, the sensing element is an interstitial glucose sensing element inserted into the body of a patient to obtain measurement data indicative of a glucose level of the interstitial fluid compartment in the body of the patient.

The computing device 102 generally represents a server or other remote device configured to receive data or other information from the sensing devices 106, 108, store or otherwise manage data in the database 104, and analyze or otherwise monitor data received from the sensing devices 106, 108 and/or stored in the database 104. In practice, the computing device 102 may reside at a location that is physically distinct and/or separate from the electronic devices 106, 108, such as, for example, at a facility that is owned and/or operated by or otherwise affiliated with a manufacturer of the sensing devices 106, 108 or other medical devices utilized in connection with the data management system 100. For purposes of explanation, but without limitation, the computing device 102 may alternatively be referred to herein as a server, a remote server, or variants thereof.

The server 102 generally includes a processing system and a data storage element (or memory) capable of storing programming instructions for execution by the processing system, that, when read and executed, cause processing system to create, generate, or otherwise facilitate the applications or software to perform or otherwise support the processes, tasks, operations, and/or functions described herein. Depending on the embodiment, the processing system may be implemented using any suitable processing system and/or device, such as, for example, one or more processors, central processing units (CPUs), graphics processing units (GPUs) controllers, microprocessors, microcontrollers, processing cores and/or other hardware computing resources configured to support the operation of the processing system described herein. Similarly, the data storage element or memory may be realized as a random access memory (RAM), read only memory (ROM), flash memory, magnetic or optical mass storage, or any other suitable non-transitory short or long term data storage or other computer-readable media, and/or any suitable combination thereof. In some embodiments, the server 102 may be implemented using a cluster of actual and/or virtual servers operating in conjunction with each other in a conventional manner (e.g., using load balancing, cluster management, and/or the like) or otherwise configured to provide a "cloud-based" virtual server system.

In exemplary embodiments, the database 104 is utilized to store or otherwise maintain patient data for a plurality of different patients. For example, the database 104 may store or otherwise maintain reference blood glucose measurements (e.g., a fingerstick or metered blood glucose value) for different patients in association with the contemporaneous or current measurement parameters output by the respective sensing device 106, 108 associated with a respective patient at or around the time of the respective blood glucose measurement. Additionally, the database 104 may maintain personal information associated with the different patients, including the respective patient's age, gender, height, weight, body mass index (BMI), demographic data, and/or other parameters characterizing the respective patient.

In the illustrated embodiment, the database 104 maintains measurement data 112 associated with previous uses of different instances of a particular make and/or model of sensing device 106, alternatively referred to herein as a template sensing device (or template sensor). In some embodiments, the make and/or model of template sensing device 106 corresponds to an established or legacy sensor design or legacy sensor configuration for which the database 104 already maintains modeling data 120 for converting measurement outputs into a calibrated measurement value, and accordingly, for purposes of explanation but without limitation, the template sensing device 106 may alternatively be referred to herein as a legacy sensing arrangement, legacy sensing device, legacy sensor or a variant thereof. In this regard, the template sensor measurement data 112 may include measurement outputs provided by the legacy sensing device 106 (e.g., sampled electrochemical signal values) that are indicative of a patient's glucose level along with contemporaneous or corresponding reference blood glucose measurements (e.g., a fingerstick or metered blood glucose value) for the patient during the time period corresponding to the sensor measurement outputs. For example, historical template sensor measurement data 112 may include data obtained from different patients during a prior clinical trial, where each patient's reference blood glucose measurements (and corresponding calibration timestamps) and measurement outputs provided by their respective instance of the legacy sensing device 106 during the trial period are maintained in association with one another (e.g., using one or more identifiers assigned to the respective patient).

In the illustrated embodiment, the database 104 also maintains measurement data 114 associated with uses of different instances of a different make and/or model of sensing device 108, that is, a make and/or model that is different from that of the template sensor 106. In some embodiments, the make and/or model of sensing device 108 corresponds to a new sensor design or new sensor configuration (e.g., a new sensing arrangement) for which the database 104 did not previously maintain modeling data 120 for converting measurement outputs into a calibrated measurement value. For purposes of explanation but without limitation, the sensing device 108 may alternatively be referred to herein as a target sensing device (or target sensor). In this regard, the target sensor measurement data 114 may include data obtained from different patients during a current, recent, or ongoing clinical trial, where each patient's reference blood glucose measurements (and corresponding calibration timestamps) and measurement outputs provided by their respective instance of the new sensing device 108 during the trial period are maintained in association.

As described in greater detail below in the context of FIG. 3, in some embodiments, the database 104 also maintains measurement data 116 associated with uses of different instances of the template sensor 106 concurrently with or contemporaneously to respective instances of the target sensor 108. For example, during a clinical trial, individual patients may wear or otherwise utilize a first instance of a template glucose sensor 106 concurrently with a second instance of a target glucose sensor 108, thereby providing different glucose measurement data sets for a common patient that were concurrently obtained using different types or configurations of glucose sensors. Thus, the measurement data 116 may include data obtained from the same patients using respective instances of the legacy sensor 106 during the current, recent, or ongoing clinical trial for the target sensor 108 concurrently with obtaining the target sensor measurement data 114, where measurement outputs provided by the respective instances of the legacy sensing device 106 during the trial period are maintained in association with the respective patient and/or the respective patient's instance of the target sensor 108, thereby allowing for correlations to be established between the different measurement outputs concurrently provided by different sensing devices 106, 108 at or around the same time for the same patient. In this regard, the relationships between the target sensor measurement data 114 and the template sensor measurement data 116 for the current clinical trial may be utilized to derive a model for translating between datasets, thereby allowing historical template sensor measurement data 112 to be translated or otherwise converted into simulated measurement data 118 for the target sensor 108. The new sensor simulated measurement data 118 may then be analyzed, either independently or in concert with the new sensor clinical measurement data 114, to derive a model for calculating or otherwise determining an estimated calibrated measurement value, such as an estimated calibrated sensor glucose measurement value, as a function of the electrochemical measurement outputs generated by an instance of the target sensor 108.

Although not illustrated in FIG. 1, to support one or more embodiments described herein, the database 104 may also store or otherwise maintain logically distinct sets of training, testing, and validation data for the different sensors 106, 108. For example, the training set of data may be utilized to train one or more models, with the test set of data being utilized to optimize the resulting model(s) and the validation set of data being utilized to validate the performance or accuracy of the model(s). In this regard, in some embodiments, the depicted sets of data 112, 114, 116 may be partitioned or otherwise logically divided into various training, testing, and/or validation subsets. In exemplary embodiments, the training, testing, and validation data sets are mutually exclusive.

In exemplary embodiments, the server 102 utilizes the simulated measurement data 118 stored in the database 104 to determine a glucose estimation model for a particular type, configuration, make and/or model of sensing element and/or sensing arrangement. Thereafter, the server 102 may store or otherwise maintain the data 120 characterizing the sensor glucose estimation model in the database 104 and subsequently provide the sensor glucose estimation model to instances of the particular type or configuration of sensing element and/or sensing arrangement. For example, upon initialization of an instance of a sensing device 106, 108, the respective sensing device 106, 108 may be configured to connect to the network 110 and download or otherwise obtain the appropriate sensor glucose estimation model from the remote server 102 via the network 110. Thereafter, a controller or other processing system of the sensing device 106, 108 may utilize the sensor glucose estimation model to determine estimated calibrated glucose measurement values for a patient independent of and/or without requiring a fingerstick measurement or other calibration procedure. In yet other embodiments, the sensor glucose estimation model may be provided to another electronic device (e.g., an infusion device or another electronic device in an infusion system) that is configured to receive measurement outputs from a sensing device 106, 108. In such embodiments, the infusion device or other electronic device may utilize the obtained sensor glucose estimation model to determine estimated calibrated glucose measurement values using measurement outputs provided by the particular sensing device 106, 108 without requiring a fingerstick measurement or other calibration procedure.

As described in greater detail below in the context of FIG. 6, in some embodiments, rather than relying on concurrent template sensor measurement data 116 (which may be absent from such embodiments), the server 102 analyzes the target sensor measurement data 114 using a generative adversarial network (GAN) or similar machine learning technique to derive a generative model representative of the electrochemical behavior of the target sensor 108. The generative model is then utilized by the server 102 to generate or otherwise emulate probabilistically the measurement outputs by theoretical instances of the target sensor 108, and thereby obtain simulated measurement data 118 that represents the expected electrochemical behavior and/or characteristics of the target sensor 108. The server 102 may then similarly utilize the simulated measurement data 118 stored in the database 104, either independently or in combination with the observed target sensor measurement data 114, to determine a glucose estimation model for a particular type, configuration, make and/or model of sensing element and/or sensing arrangement.

It should be appreciated that FIG. 1 is a simplified representation of a data management system 100 for purposes of explanation and is not intended to be limiting. In this regard, in practice, various aspects of data storage and/or data processing described herein in the context of the server 102 and/or the database 104 could equivalently be implemented on or at a sensing device 106, 108. For example, the sensing device 106, 108 may implement or otherwise support a file system, an object store, or the like to store or otherwise maintain measurement data or other reference data, which in turn, may be analyzed by or at the sensing device 106, 108 to generate training data, modeling data, calibration data, and/or the like. That said, for purposes of explanation, the subject matter may be described primarily in the context of data storage at the database 104 with data processing performed by or at the server 102.

Figure 2:
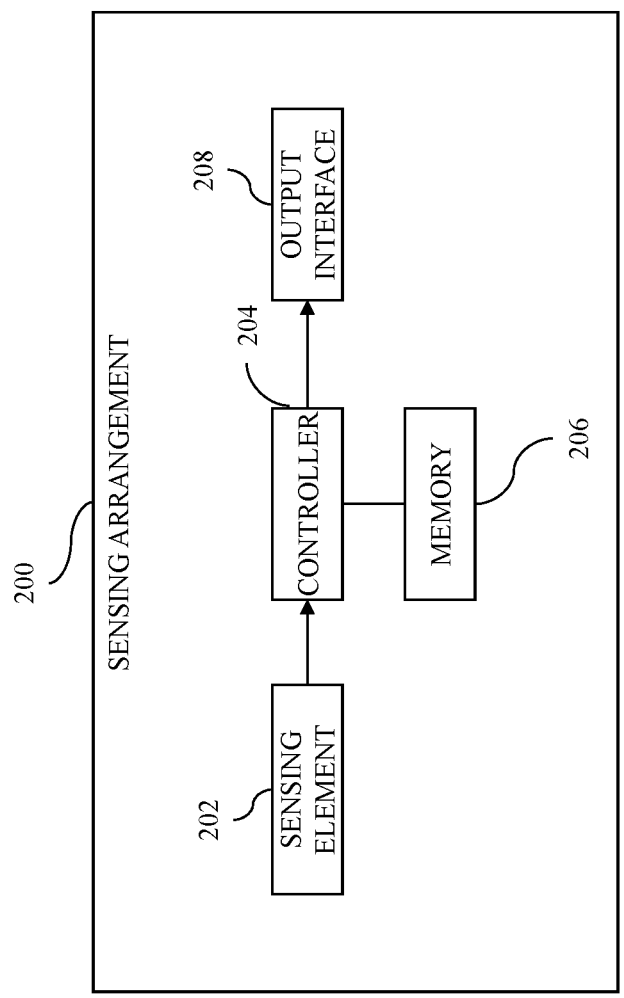
FIG. 2 is a block diagram of an exemplary embodiment of a sensing arrangement suitable for use in the data management system of FIG. 1.

FIG. 2 depicts an exemplary embodiment of a sensing arrangement 200 suitable for use in the data management system 100 of FIG. 1 (e.g., as one or more of sensing devices 106, 108). in accordance with one or more embodiments. The illustrated sensing device 200 includes, without limitation, a controller 204, a sensing element 202, an output interface 208, and a data storage element (or memory) 206. The controller 204 is coupled to the sensing element 202, the output interface 208, and the memory 206, and the controller 204 is suitably configured to support the operations, tasks, and/or processes described herein.

The sensing element 202 generally represents the component of the sensing device 200 that is configured to generate, produce, or otherwise output one or more electrical signals indicative of a condition that is sensed, measured, or otherwise quantified by the sensing device 200. In this regard, the physiological condition of a user influences a characteristic of the electrical signal output by the sensing element 202, such that the characteristic of the output signal generated by the electrochemical response of the sensing element 202 corresponds to or is otherwise correlative to the physiological condition that the sensing element 202 is sensitive to. In exemplary embodiments, the sensing element 202 is realized as an interstitial glucose sensing element that generates or otherwise provides one or more output electrical signals having a current, voltage, or other characteristic associated therewith that is correlative to the interstitial fluid glucose level that is sensed or otherwise measured in the body of the patient by the sensing arrangement 200. For example, the output measurement parameters generated or otherwise provided by the electrochemical response of the glucose sensing element 202 may include an electrical current generated by the sensing element 202 in response to a glucose concentration (alternatively referred to as an isig value), one or more electrochemical impedance spectroscopy (EIS) values (for one or more frequencies) or other measurements indicative of a characteristic impedance associated with the sensing element 202 in response to a glucose concentration, a counter electrode voltage (Vctr) (e.g., the difference between counter electrode potential and working electrode potential), and/or the like. That said, it should be noted that the subject matter described herein is not limited to signals indicative of a physiological condition and could be implemented in an equivalent manner for sensing elements generating signals indicative of non-physiological conditions.

In some embodiments, the sensing element 202 is replaceable or interchangeable within the sensing arrangement 200. For example, a patient may periodically replace an interstitial glucose sensing element (e.g., every 3 days) and reinsert the new interstitial glucose sensing element at the same or different location on the patient's body (alternatively referred to as a site location). In this regard, in such embodiments, measurement data obtained from the sensing arrangement 200 and/or sensing element 202 may be associated with a particular instance of the sensing element 202 and/or the particular sensor site location utilized with that respective instance of the sensing element 202 for purposes of analyzing performance with respect to the age or site location of the sensing element 202. In the context of such embodiments, sensor age should be understood as referring to the amount or duration of time for which an instance of the sensing element 202 has been in use from the initial time of insertion.

Still referring to FIG. 2, the controller 204 generally represents the processing system or other hardware, circuitry, logic, firmware and/or other component(s) of the sensing device 200 that is coupled to the sensing element 202 to receive the electrical signals output by the sensing element 202 and perform various additional tasks, operations, functions and/or processes described herein. For example, the controller 204 may filter, analyze or otherwise process the electrical signals received from the sensing element 202 to obtain a calibrated measurement of the interstitial fluid glucose level. In one or more embodiments, the sensing device 200 comprises an instance of the target sensor 108, and the controller 204 utilizes a glucose estimation model derived using the simulated measurement data 118 for the target sensor 108 to calculate or otherwise determine an effectively-calibrated sensor glucose measurement value as a function of the output measurement parameters (e.g., electrical current output, counter electrode voltage, electrochemical impedance, and the like) provided by the sensing element 202 of the instance of the target sensor 108. In this regard, function, equation, and/or other data for the model associated with the sensing element 202 may be stored or otherwise maintained in the memory 206 and downloaded from or otherwise provided by the remote server 102, as described in greater detail below.

Depending on the embodiment, the controller 204 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software executed by the controller 204, or in any practical combination thereof. In exemplary embodiments, the controller 204 includes or otherwise accesses the data storage element or memory 206. The memory 206 may be realized using any sort of RAM, ROM, flash memory, registers, hard disks, removable disks, magnetic or optical mass storage, short or long term storage media, or any other non-transitory computer-readable medium capable of storing programming instructions, code, or other data for execution by the controller 204. The computer-executable programming instructions, when read and executed by the controller 204, cause the controller 204 to perform the tasks, operations, functions, and processes described in greater detail below.

In some embodiments, the controller 204 includes an analog-to-digital converter (ADC) or another similar sampling arrangement that samples or otherwise converts the output electrical signal(s) received from the sensing element 202 into corresponding digital measurement data value(s) correlative to the interstitial fluid glucose level sensed by the sensing element 202. In other embodiments, the sensing element 202 may incorporate an ADC and output a digital measurement value. In one or more embodiments, the current of the electrical signal output by the sensing element 202 is influenced by the user's interstitial fluid glucose level, and the digital measurement data value is realized as a current measurement value provided by an ADC based on an analog electrical output signal from the sensing element 202.

The output interface 208 generally represents the hardware, circuitry, logic, firmware and/or other components of the sensing arrangement 200 that are coupled to the controller 204 for outputting data and/or information from/to the sensing device 200, for example, to/from the remote server 102 or another device on the network 110. In this regard, in exemplary embodiments, the output interface 208 is realized as a communications interface configured to support communications to/from the sensing device 200. In such embodiments, the communications interface 208 may include or otherwise be coupled to one or more transceivers or communication devices capable of supporting wireless communications between the sensing device 200 and another electronic device (e.g., an infusion device or another electronic device in an infusion system). Alternatively, the communications interface 208 may be realized as a port that is adapted to receive or otherwise be coupled to a wireless adapter that includes one or more transceivers and/or other components that support the operations of the sensing device 200 described herein. In other embodiments, the communications interface 208 may be configured to support wired communications to/from the sensing device 200. In yet other embodiments, the output interface 208 may include or otherwise be realized as an output user interface element, such as a display element (e.g., a light-emitting diode or the like), a display device (e.g., a liquid crystal display or the like), a speaker or another audio output device, a haptic feedback device, or the like, for providing notifications or other information to the user. In such embodiments, the output user interface 208 may be integrated with the sensing arrangement 200 (e.g., within a common housing) or implemented separately.

It should be understood that FIG. 2 is a simplified representation of a sensing device 200 for purposes of explanation and is not intended to limit the subject matter described herein in any way. In this regard, although FIG. 2 depicts the various elements residing within the sensing device 200, one or more elements of the sensing device 200 may be distinct or otherwise separate from the other elements of the sensing device 200. For example, the sensing element 202 may be separate and/or physically distinct from the controller 204 and/or the communications interface 208. Furthermore, features and/or functionality of described herein as implemented by the controller 204 may alternatively be implemented at another device within an infusion system.

Figure 3:
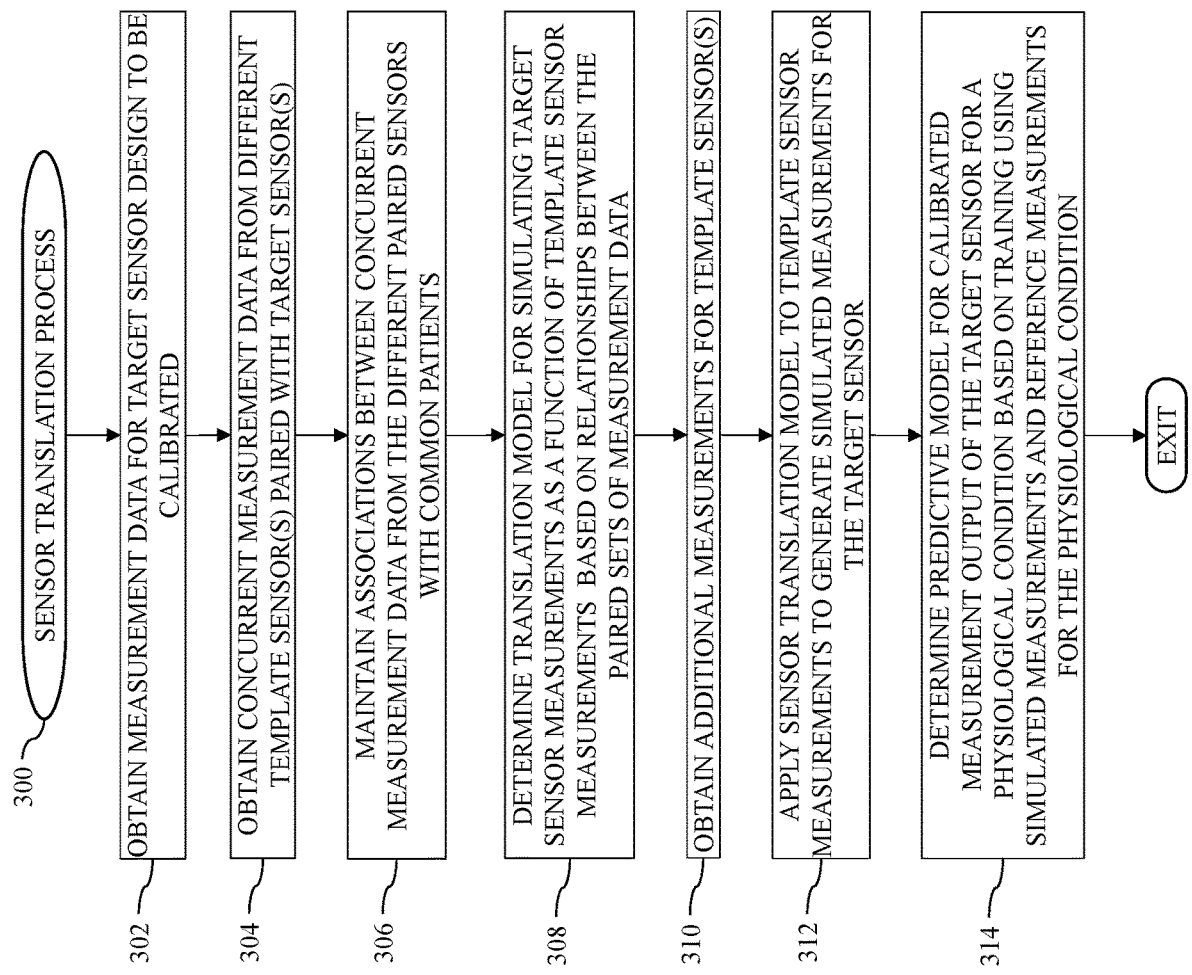
FIG. 3 is a flow diagram of an exemplary sensor translation process suitable for use with the data management system of FIG. 1 in one or more exemplary embodiments.

FIG. 3 depicts an exemplary embodiment of a sensor translation process 300 for developing a model for estimating a calibrated output of a sensing arrangement using simulated measurement data obtained by translating measurement data from a different sensing arrangement. The various tasks performed in connection with the sensor translation process 300 may be performed by hardware, firmware, software executed by processing circuitry, or any combination thereof. For illustrative purposes, the following description may refer to elements mentioned above in connection with FIGS. 1-2. It should be appreciated that the sensor translation process 300 may include any number of additional or alternative tasks, the tasks need not be performed in the illustrated order and/or the tasks may be performed concurrently, and/or the sensor translation process 300 may be incorporated into a more comprehensive procedure or process having additional functionality not described in detail herein. Moreover, one or more of the tasks shown and described in the context of FIG. 3 could be omitted from a practical embodiment of the sensor translation process 300 as long as the intended overall functionality remains intact.

The illustrated sensor translation process 300 begins by receiving or otherwise obtaining measurement data for the particular type or configuration of sensing arrangement to be modeled (task 302). For example, as described above, instances of a target sensor 108 may be provided to a number of different individuals or patients as part of a clinical trial. In this regard, the target sensor measurement data 114 includes or otherwise maintains, for each individual or patient, the measurement parameters (e.g., output electrical current, counter electrode voltage, electrochemical impedance, and the like) that were generated, output, measured, or otherwise obtained by the sensing element 202 of the respective sensor 108 being used by the patient during the clinical trial. The target sensor measurement data 114 may also maintain calibration data associated with the respective patient (e.g., timestamped reference blood glucose measurements and corresponding calibration factors) and/or other data associated with the respective patient (e.g., demographic data and/or the like).

The sensor translation process 300 also receives or otherwise obtains concurrent measurement data for a different type or configuration of sensing arrangement that is paired with a respective instance of the sensing arrangement to be calibrated and maintaining associations between the different sets of concurrent measurement data (tasks 304, 306). For example, during the clinical trial, instances of a template sensor 106 may be provided to the same individuals or patients that are part of the clinical trial for use concurrently with their respective instance of the target sensor 108. Similar to the target sensor measurement data 114, the template sensor measurement data 116 also includes or otherwise maintains, for each individual or patient, the measurement parameters (e.g., output electrical current, counter electrode voltage, electrochemical impedance, and the like) that were generated, output, measured, or otherwise obtained by the sensing element 202 of the respective template sensor 106 being used by the patient during the clinical trial. The template sensor measurement data 116 and the target sensor measurement data 114 may each be stored or maintained using one or more unique patient identifiers that allows the remote server 102 to correlate measurements for the same patient across the different sensors 106, 108. Additionally, the samples that make up the template sensor measurement data 116 and the target sensor measurement data 114 may be timestamped to allow the sensor translation process 300 to temporally associate measurement samples for the same patient across the different sensors 106, 108.

Still referring to FIG. 3, the sensor translation process 300 continues by calculating or otherwise determining a predictive model for generating simulated measurement data for use in developing a calibration algorithm for the target sensor based at least in part on the relationships between the paired data sets (task 308). In this regard, based on the relationship between the target (or new) sensor measurement data and the concurrent or contemporaneous template (or legacy) sensor measurement data for each patient, a sensor data translation model is derived for translating historical legacy sensor measurements to probable measurement values that would likely be output or generated by the target sensor 108 having a new or different design or configuration for the given glucose dynamics that resulted in the respective historical legacy sensor measurements. That is, the template sensor measurement data 116 provides the input variable combinations by which the synthetic data algorithms translate template sensor measurement values into temporally associated simulated target sensor measurement data 118.

In some embodiments, for each different measurement parameter to be output by the target sensor 108 (e.g., electrical current output, counter electrode voltage, electrochemical impedance, and the like), analytical, machine learning, or artificial intelligence techniques are utilized to determine which combination of measurement parameters output by the template sensor 106 are correlated to or predictive of the respective measurement parameter based on the relationships between the paired sets of observed template measurement parameter values and observed measurement parameter value for each of the patients for which paired concurrent measurement data 114, 116 is maintained. Additionally, the remote server 102 may utilize analytical, machine learning, or artificial intelligence techniques to identify other contextual or non-measurement variables that may be relevant to modeling the measurement parameter of interest, such as, for example, the patient's age, gender, or other demographic attributes. For example, non-measurement variables may be utilized to augment training of models to achieve better dataset balance, exclude irrelevant data, and/or perform other pre-processing techniques. The remote server 102 may then determine a corresponding equation, function, or model for calculating a probable or expected measurement parameter value to be generated by the target sensor 108 based on the correlative subset of legacy sensor measurement parameters (e.g., isig, EIS, Vctr, and/or the like) that are input variables to the model. Thus, the sensor data translation model is capable of characterizing or mapping a particular combination of template sensor measurement parameter values to a probable measurement parameter value for the target sensor 108.

In one embodiment, a shifting translation technique is utilized to derive the sensor data translation model based on population statistics as a function of electrical current output, counter electrode voltage, electrochemical impedance, and time from sensor connection. That is, the sensor data translation model may map a particular combination of electrical current output, electrode voltage and/or electrochemical impedance measurement values obtained via a template sensor 106 to a probable measurement value that would be produced by the target sensor 108 for one or more of the electrical current output, electrode voltage and/or electrochemical impedance. Using the shifting translation technique, the translation model is generated by minimizing the error between the template sensors 116, after the signal has been transformed, and the paired template sensors 114. Error between the transformed template sensor and target sensor may be calculated as difference in means of signal distributions, mean of difference between each paired sensor reading, or similar calculation. In this regard, the translation model minimizes the error between the distribution of the template sensor signal (e.g., the sequential template sensor measurement values) shifted by the model equation and the distribution of the target sensor signal (e.g., the sequential target sensor measurement values). Possible model equations include but are not limited to polynomial functions, logistic functions, and sigmoidal functions, etc. In this regard, those skilled in the art will appreciate that various different potential shifting techniques and possible model equations exist, and the details of any particular implementation are not germane to this detailed description.

In another embodiment, a concatenative translation technique is utilized to derive the translation model between template sensor 106 and target sensor 108 as a function of electrical current output, counter electrode voltage, electrochemical impedance, time from sensor connection, blood glucose reference measurements, and sensor calibration data from paired template sensor trial data 116 and target sensor trial data 114. The concatenative translation technique segments each signal from the template sensor trial data 116 and the target sensor trial data 114 into signal units (signits) to generate a paired library. To translate template sensor data 112, the template sensor data 112 is similarly processed into signits. For each signit in the template sensor data 112, a nearest neighbor match is identified from the library by matching to signits generated from the template sensor trial data 116. The match is identified by minimizing a cost function with match and concatenation penalties, where the calibration data is used to maintain specified signal-to-calibration data relationships. Once the match is found, the corresponding paired signit from the target sensor trial data 114 to the identified matched signit from the template sensor data 112 is used for concatenation. This matching process is repeated for all signits across the template sensor data 112 to identify a series of signits from the best match target sensor trial data 114 to concatenate into the full translated signal. The concatenation algorithm can be configurable to allow adjustments to the signit length, the degree of adjacent signit overlap length, the range of time from sensor connection for signits in the library, the featurization method, data transformation methods, and match and concatenation cost function definitions.

In yet another embodiment, a deep neural network translation technique is utilized to derive the sensor data translation model as a function of electrical current output, counter electrode voltage, electrochemical impedance, and time from sensor connection from paired template sensor trial data 116 and target sensor trial data 114. The input data is processed to adjust data input size (segment length), length of adjacent segment overlap (e.g. 50%), a time series smoothing parameter (e.g. 3-to-1, centered or trailing smoothing), window region to filter a specific time from sensor connection for training (e.g. days 2-5), and data transformation methods (e.g. standardization or normalization). The processed paired data from the template sensor trial data 116 and the target sensor trial data 114 is used to train a deep feed-forward neural network with fully connected layers and regularization. The neural network is configurable based on the number of hidden layers, the width of hidden layers, the activation function per layer, the loss function (e.g. mean squared error (MSE), root mean squared error (RMSE), mean absolute percentage error (MAPE), or the like), least absolute shrinkage and selection operator (LASSO) and Ridge regularization parameters, learning rate, training batch size, and number of training epochs. During translation, the processed query template sensor data 112 is translated by the trained neural network into the target sensor data 118.

Still referring to FIG. 3, after deriving the sensor data translation model based on the relationship between paired measurement data sets, the sensor translation process 300 retrieves or otherwise obtains historical measurement data for the template (or legacy) sensor and utilizes the sensor data translation model to calculate or otherwise determine simulated measurement data for the target (or new) sensor by translating measurement data from one sensor design into another sensor design (tasks 310, 312). In this regard, the sensor data translation model may be applied to a set of historical measurement data that was previously obtained using an instance of the template sensor 106 to convert measurement values of that historical legacy sensor measurement data set into a different set of measurement values that represent the probable electrochemical behavior of the target sensor 108 to the same stimulus or conditions that produced the respective set of historical measurement data. For example, if the database 104 maintains historical legacy sensor clinical trial measurement data 112 for 4000 different patients, the remote server 102 may retrieve the respective data set for each individual patient, apply the sensor data translation model to the respective data set for each individual patient to generate a simulated measurement data set for that patient, and store the simulated measurement data set associated with the target sensor 108 in the database 104, resulting in 4000 patient sets of simulated measurement data 118 for the target sensor 108 without actually requiring those 4000 different patients to have worn or utilized the target sensor 108. In this manner, historical measurement data 112 from previous clinical trials may be mapped to a new model, make, type, and/or configuration of sensing device 108 to effectively increase the amount of available clinical trial data for the new model, make, type, and/or configuration of sensing device 108 without requiring patients engage in such a trial.

After generating simulated measurement data for the particular type or configuration of sensing arrangement to be calibrated, the sensor translation process 300 continues by calculating or otherwise determining a glucose estimation model for predicting the patient's glucose level as a function of the measurement parameters output by the sensing arrangement using the simulated measurement data (task 314). In exemplary embodiments, the remote server 102 may create an augmented set of measurement data for the target sensor 108 by combining the observed target sensor clinical trial measurement data 114 with the simulated measurement data 118 for the target sensor 108 to increase the size of the data set. For example, the observed target sensor clinical trial measurement data 114 may be obtained for a fewer number of patients than the number of patient sets of simulated measurement data 118, thereby reducing the time or costs associated with the clinical trial for the target sensor 108, while the simulated measurement data 118 provides a larger or more robust data set for deriving the glucose estimation model to maintain the performance of the efficacy of the glucose estimation model even though the number of trial patients may be reduced. That said, in some embodiments, the glucose estimation model could be derived solely based on the simulated measurement data 118.

In exemplary embodiments, the glucose estimation model is utilized to generate an estimated sensor glucose value as a function of one or more measurement parameters (e.g., output electrical current, counter electrode voltage, electrochemical impedance, and the like). For example, a training data set for the glucose estimation model may be created by the remote server 102 identifying and obtaining the reference blood glucose measurement values associated with the calibration data points for the various patient data sets of the historical template sensor measurement data 112 that were translated into simulated measurement data 118 and utilizing the timestamps and patient identifiers associated with those reference blood glucose measurement values to identify simulated measurement parameter values temporally associated with or otherwise corresponding to that calibration data point, with the reference blood glucose measurement values functioning as the output variable of the training data set and the simulated measurement parameter values functioning as the input variable combinations corresponding to the respective blood glucose measurement values. Similarly, the remote server 102 may identify and obtain the reference blood glucose measurement values associated with the calibration data points for the patient data sets of the observed target sensor measurement data 114 and utilize the timestamps and patient identifiers to identify the temporally associated measurement parameter values corresponding to that calibration data point for use as additional combinations of output variable value and input variable combinations, respectively, for the training data set.

In exemplary embodiments, the remote server 102 utilizes machine learning techniques, such as genetic programming (GP), artificial neural network (NN), regression decision tree (DT), and/or the like to derive a glucose estimation model for predicting or estimating the patient's interstitial glucose measurement value to which the output measurement parameters of the target sensor 108 most likely corresponds as a function of the measurement parameters based on the relationships between the reference blood glucose measurement values and the respective combinations of measurement parameter values. In some embodiments, the estimated sensor glucose value derived using the glucose estimation model is fused or otherwise combined with one or more other values (e.g., a current sensor glucose measurement determined using a calibration factor) to arrive at a final sensor glucose measurement value that is output or otherwise provided to other devices or components for other uses (e.g., generating notifications, adjusting insulin delivery, etc.). In this regard, the estimated sensor glucose value may augment or otherwise adjust the normal sensor glucose measurement value determined using a calibration factor in a manner that accounts for variability in the accuracy or reliability of the calibration factor with respect to time. Examples of using machine learning to derive sensor glucose models and determining estimated sensor glucose values are described in greater detail in U.S. Patent Application Pub. No. 2019/0076066.

In exemplary embodiments, after determining the glucose estimation model for the target sensor 108, the remote server 102 may store or otherwise maintain the data defining the glucose estimation model in the database 104 (e.g., modeling data 120) in association with the target sensor 108. In some embodiments, the remote server 102 may automatically push or otherwise provide the glucose estimation model to various instances of the target sensor 108 on the network 110 or to other electronic devices that are used in connection with the target sensor 108 (e.g., fluid infusion devices, mobile devices, and/or the like). In other embodiments, upon deployment, a new instance of the target sensor 108 may automatically download the glucose estimation model from the remote server 102 via the network 110. The glucose estimation model is then utilized in connection with the deployed instances of the target sensor 108 to determine estimated sensor glucose measurement values that may influence insulin delivery, patient alerts or notifications, and/or the like.

Figure 4:
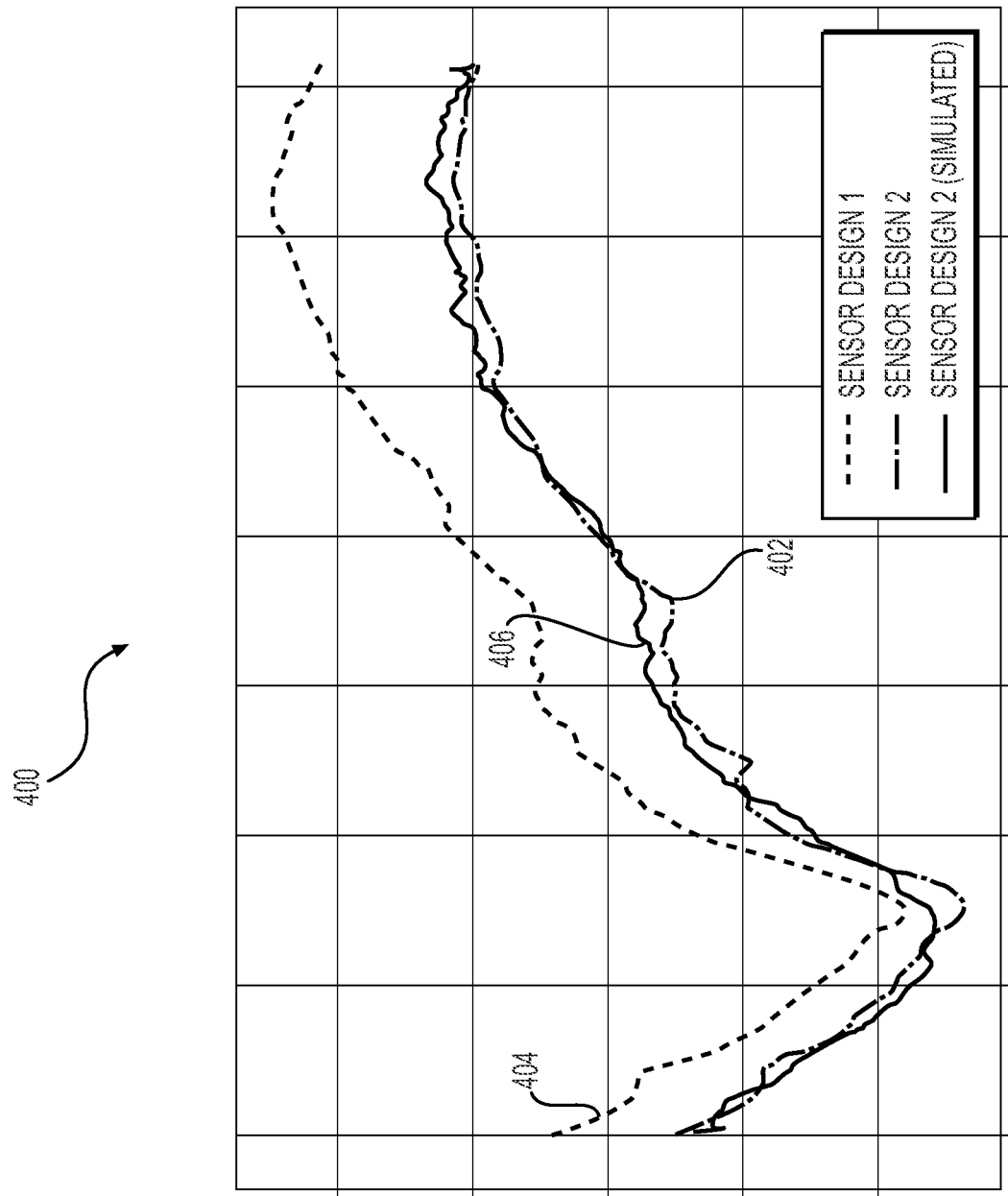
FIG. 4 is a graph depicting relationships between observed sensor measurement data and simulated sensor measurement data in connection with an exemplary embodiment of the sensor translation process of FIG. 3.

FIG. 4 depicts a graph 400 illustrating an exemplary relationship between an observed measurement parameter 402 (e.g., isig, EIS, Vctr, or the like) with respect to time obtained using an instance of a sensor to be modeled (e.g., target sensor 108) and the same observed measurement parameter 404 with respect to time that is concurrently obtained using an instance of a different sensor for which translation between the two sensors is desired (e.g., template sensor 106). For example, with reference to FIG. 1, graph line 402 may depict the observed electrical current (isig) output by an instance of the target sensor 108 during a clinical trial for a patient that was concurrently using an instance of the template sensor 106, with the graph line 404 depicting the observed electrical current (isig) output by the instance of the template sensor 106 during the clinical trial. In this regard, the graph lines 402, 404 correspond to concurrent measurement data obtained for the same patient using the different instances of sensors 106, 108 (e.g., a first instance of a template sensing arrangement 106 and a second instance of a target sensing arrangement 108). In one embodiment, the target sensor measurement data 402 for the patient may correspond to an entry in the target sensor clinical trial measurement data set (e.g., data 114) maintained by the database 104 while the template sensor measurement data 404 for the patient corresponds to an entry in the template sensor clinical trial measurement data set (e.g., data 116) maintained by the database 104, with an identifier associated with the patient being utilized to associated or otherwise correlate the entries with one another. As described above, the relationships between the target sensor clinical trial measurement data 114 and the template sensor clinical trial measurement data 116 is analyzed by the remote server 102 using machine learning to obtain a sensor translation model for translating measurement data from the legacy sensor domain to the new sensor domain. In the graph 400 depicted in FIG. 4, graph line 406 represents the predicted electrical current (isig) output for the instance of the target sensor 108 that is calculated by applying the sensor translation model to the template sensor measurement data 404. Thus, the predicted target sensor measurement data 406 represents the expected electrochemical response and corresponding electrical current (isig) output that would likely be generated by the instance of the target sensor 108 in response to the same interstitial fluid glucose levels that resulted in the output 404 generated by the template sensor 106. As described above, the simulated measurement data set represented by line 406 may be included in the training data set used to derive the sensor glucose estimation model for the target sensor 108.

Figure 5:
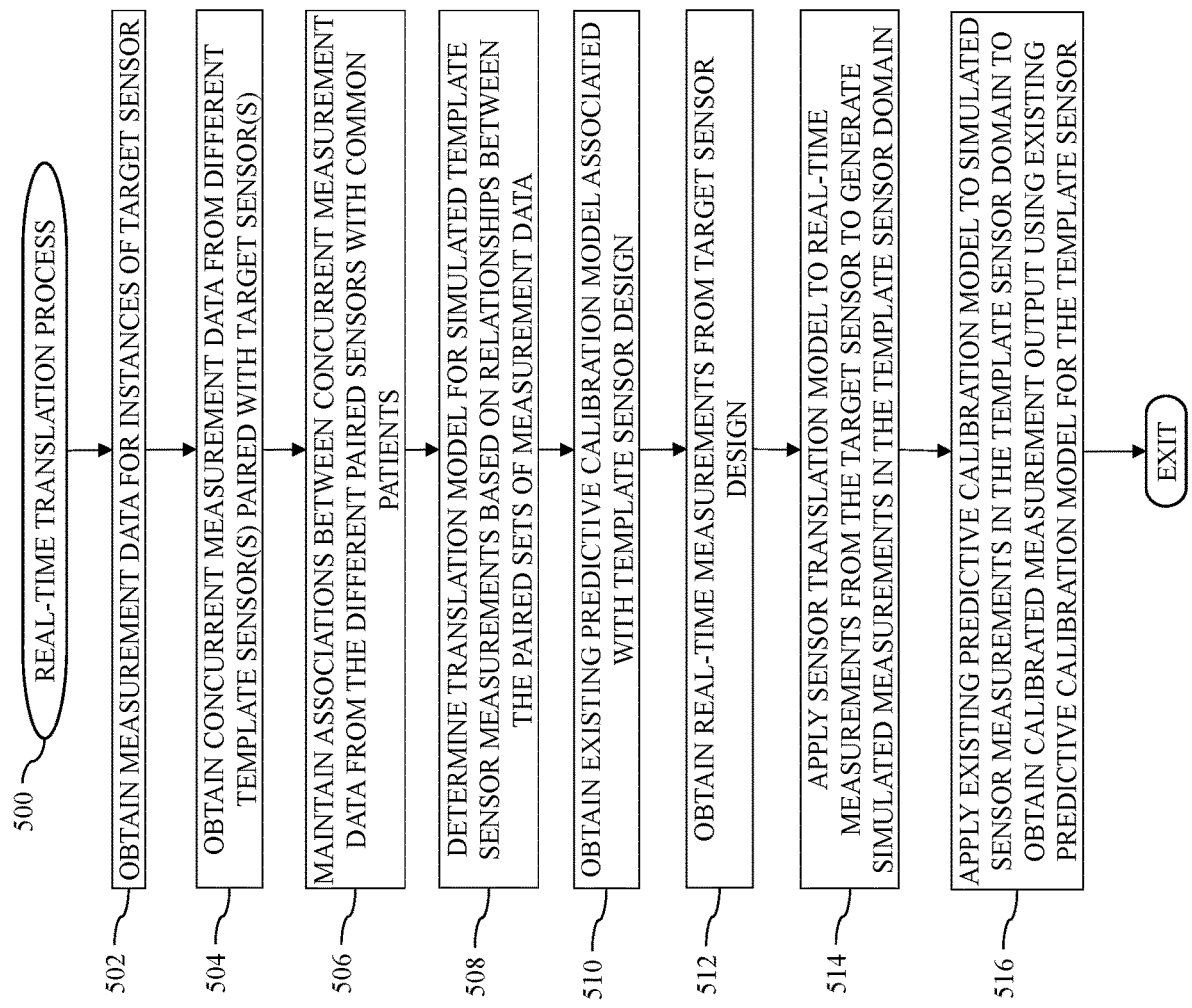
FIG. 5 is a flow diagram of an exemplary real-time translation process suitable for use with the data management system of FIG. 1 in one or more exemplary embodiments.

FIG. 5 depicts an exemplary embodiment of a real-time translation process 500 for using a sensor data translation model to leverage a calibration algorithm associated with one design, type or configuration of sensor with measurements output by a different design, type or configuration of sensor. For example, an existing (or legacy) calibration algorithm previously developed for a template (or legacy) sensor may be utilized to determine estimated calibrated measurement values in real-time using the existing calibration algorithm in connection with an instance of a target (or new) sensor, which may be alternatively referred to herein as a backwards translation process (e.g., by translating measurement output from a new sensor effectively "backwards" in time to an older sensor domain). In this regard, the backwards translation process may be used to leverage a legacy calibration algorithm for a new sensor without retraining the legacy algorithm or requiring development of a calibration algorithm for the new sensor. Conversely, the real-time translation process 500 could also be performed in an equivalent manner to leverage a new or more recently developed calibration algorithm for a new sensor with a legacy sensor to determine estimated calibrated measurement values in real-time using the new calibration algorithm in connection with an instance of the legacy sensor, which may alternatively be referred to herein as a forwards translation process (e.g., by translating measurement output from an older legacy sensor effectively "forwards" in time to a newer sensor domain).

The various tasks performed in connection with the real-time translation process 500 may be performed by hardware, firmware, software executed by processing circuitry, or any combination thereof. For illustrative purposes, the following description may refer to elements mentioned above in connection with FIGS. 1-2. It should be appreciated that the real-time translation process 500 may include any number of additional or alternative tasks, the tasks need not be performed in the illustrated order and/or the tasks may be performed concurrently, and/or the real-time translation process 500 may be incorporated into a more comprehensive procedure or process having additional functionality not described in detail herein. Moreover, one or more of the tasks shown and described in the context of FIG. 5 could be omitted from a practical embodiment of the real-time translation process 500 as long as the intended overall functionality remains intact.

The real-time translation process 500 obtains concurrent measurement data for different sensors, maintains associations between the measurement data, and determines a predictive translation model for generating simulated measurement data in one sensor domain as a function of measurement data from the other sensor domain based at least in part on the relationships between the paired data sets (tasks 502, 504, 506, 508) in a similar manner as described above in the context of the translation modeling process 300 of FIG. 3 (e.g., tasks 302, 304, 306, 308), and such common aspects will not be described herein in the context of FIG. 5. As described above, depending on the embodiment, the translation model may be determined for translating from the template sensor domain to the target sensor domain or vice versa. For purposes of explanation, the sensor domain that the real-time translation process 500 is utilized to translate measurement values into in real-time may alternatively be referred to herein as the destination sensor domain, while the other sensor domain may alternatively be referred to as the initiating sensor domain. In this regard, the sensor translation model developed for the real-time translation process 500 is provided to instances of sensors associated with the initiating sensor domain for real-time translation of measurement values into the destination sensor domain.

As described in greater detail below, the real-time translation process 500 receives or otherwise obtains the existing predictive calibration model associated with the destination sensor domain, receives or otherwise obtains real-time measurements in the initiating sensor domain, and applies the translation model to translate the real-time measurements from the initiating sensor domain into corresponding simulated measurement values in the destination sensor domain (tasks 510, 512, 514). Thereafter, the real-time translation process 500 applies the existing predictive calibration model associated with the destination sensor domain to the simulated real-time measurements to obtain a calibrated measurement output for an instance of the initiating sensor design using the existing calibration model associated with the destination sensor domain (task 516).

For example, for so-called backwards translation where measurement values from a new sensor design or configuration corresponding to target sensor 108 are translated into a domain associated with an older or legacy sensor design or configuration corresponding to template sensor 106, the real-time translation process 500 is performed to develop a model for translating from the target sensor domain to the legacy template sensor domain (e.g., tasks 502, 504, 506, 508) in a similar manner as described above. The translation model may then be pushed or otherwise provided to instances of the target sensor 108 for use with measurement values in real-time. In this regard, with reference to FIGS. 1-2, the translation model is implemented on the target sensing device 108, 200 (e.g., by controller 204) for real-time translation of measurements captured via the sensing element 202 of a new sensor design or configuration into simulated measurements in a legacy sensor domain (e.g., tasks 512, 514), thereby translating the measurement signals, such as electrical current output, voltage, and impedance obtained via the sensing element 202 of the new sensor into a domain that more closely mimics the sensor signals the legacy calibration algorithm was trained on. The simulated measurement values in the legacy sensor domain are then input or otherwise provided to the calibration model associated with the template sensor 106 to obtain a predicted or estimated calibrated measurement value for the target sensing device 108, 200 using the legacy calibration algorithm. In this regard, the target sensing device controller 204 may receive or otherwise obtain the legacy calibration model (e.g., from the server 102) and apply the legacy calibration model to sampled measurement values from sensing element 202 after translating those measurement samples into the legacy sensor domain to calculate or otherwise determine a calibrated glucose measurement value according to the legacy calibration algorithm that may be output by the target sensor 108, 200 (e.g., via output interface 208). Thus, a target sensor 108 with a new design or configuration could be deployed without a new calibration algorithm being trained or developed for the target sensor 108, but rather, estimated or predicted calibrated measurement outputs may be obtained in accordance with an existing calibration algorithm, thereby allowing well performing algorithms established for other sensors to be deployed in connection with other sensors.

In one or more embodiments, the glucose estimation model associated with a legacy or template sensor is derived or otherwise trained using measurement data obtained from instances of the legacy sensor and then stored or otherwise maintained by the remote server 102 in the database 104 for subsequent deployment to other sensor devices. Similarly, the remote server 102 may derive or otherwise determine translation models for translating between the new or target sensor domain and the legacy sensor domain and maintain those models in the database 104 as described above. Accordingly, in such embodiments, the controller 204, 722 (e.g., as discussed in further detail below with reference to FIG. 7) associated with an instance of a target sensor 108, 200, 702 may download or otherwise obtain, from the remote server 102 via a network 110, the glucose estimation model associated with the legacy sensor 106 along with the sensor translation model for translating from the new sensor domain to the legacy sensor domain. In this regard, the controller 204, 722 may then merely apply the downloaded sensor translation model to the sampled measurement outputs of the sensing element 202 to obtain simulated measurement data in the legacy sensor domain, and then apply the downloaded glucose estimation model to the simulated measurement data in the legacy sensor domain to obtain estimated glucose values based on the sampled measurement outputs of the sensing element 202. The estimated glucose values may then be output or otherwise provided by the controller 204, 722 via the output interface 208 for presentation to a user (e.g., via a display device or other graphical user interface) or analysis, collection, and/or other action by another device (e.g., an infusion device, a remote server, and/or the like).

Similarly, for so-called forwards translation where measurement values from a legacy sensor design or configuration corresponding to template sensor 106 are translated into a domain associated with a newer sensor design or configuration corresponding to target sensor 108, the real-time translation process 500 is performed to develop a model for translating from the template sensor domain to the target sensor domain (e.g., tasks 502, 504, 506, 508) in an equivalent manner as described above in the context of FIG. 3. The translation model may then be pushed or otherwise provided to instances of the template sensor 106 for use with measurement values in real-time. In this regard, with reference to FIGS. 1-2, the translation model may be implemented on the template sensing device 106, 200 (e.g., by controller 204) for real-time translation of measurements captured via the sensing element 202 of a legacy sensor design or configuration into simulated measurements in a new sensor domain (e.g., tasks 512, 514). The simulated measurement values in the new sensor domain are then input or otherwise provided to the calibration model associated with the target sensor 108 to obtain a predicted or estimated calibrated measurement value for the template sensing device 106, 200 using the newer calibration algorithm. In this regard, rather than retraining or updating a legacy sensor calibration algorithm, a newer or better performing calibration algorithm trained or developed for the target sensor 108 may be propagated back to legacy template sensors 106, thereby allowing well performing algorithms established for newer sensors to be deployed in connection with older sensors.

Figure 6:
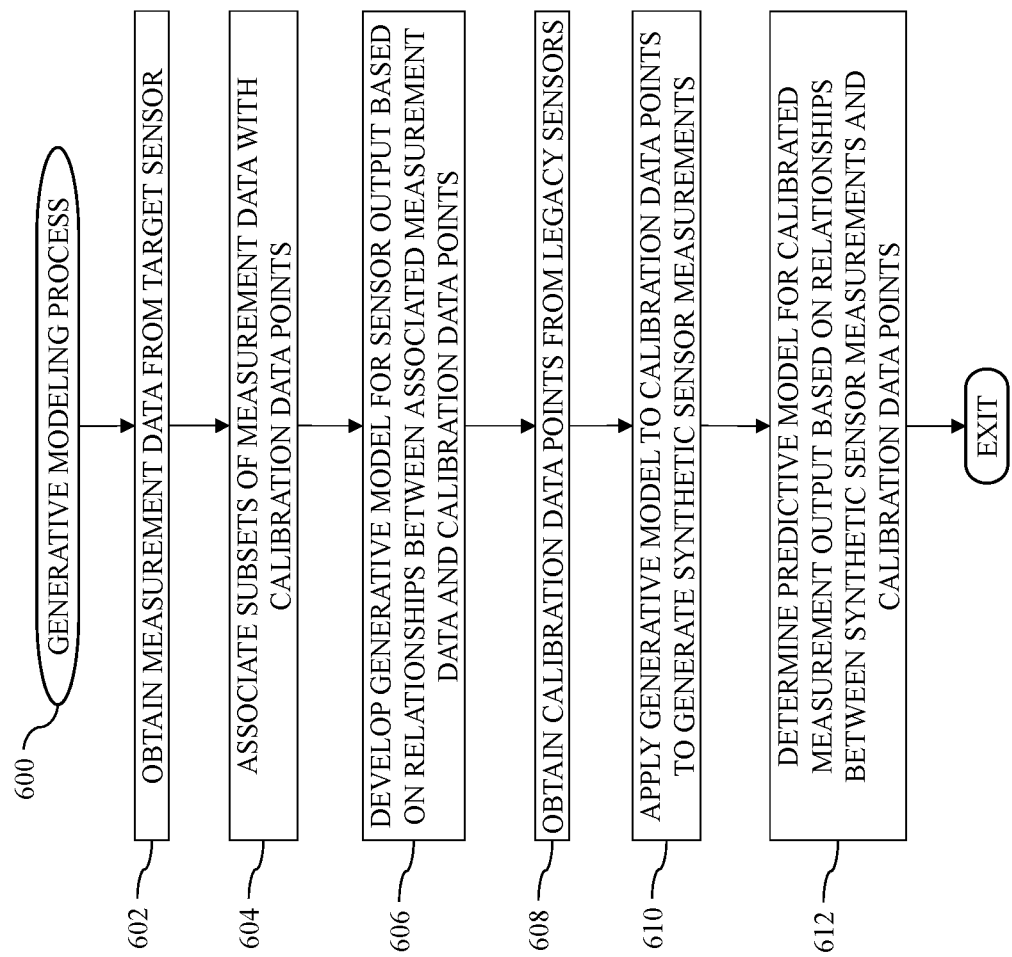
FIG. 6 is a flow diagram of an exemplary generative modeling process suitable for use with the data management system of FIG. 1 in one or more exemplary embodiments.

FIG. 6 depicts an exemplary embodiment of a generative modeling process 600 for developing a model for estimating a calibrated output of a sensing arrangement using simulated measurement data. The various tasks performed in connection with the generative modeling process 600 may be performed by hardware, firmware, software executed by processing circuitry, or any combination thereof. For illustrative purposes, the following description may refer to elements mentioned above in connection with FIGS. 1-2. It should be appreciated that the generative modeling process 600 may include any number of additional or alternative tasks, the tasks need not be performed in the illustrated order and/or the tasks may be performed concurrently, and/or the generative modeling process 600 may be incorporated into a more comprehensive procedure or process having additional functionality not described in detail herein. Moreover, one or more of the tasks shown and described in the context of FIG. 6 could be omitted from a practical embodiment of the generative modeling process 600 as long as the intended overall functionality remains intact.

The illustrated generative modeling process 600 initializes by receiving or otherwise obtaining measurement data for the particular type or configuration of sensing arrangement to be modeled (task 602). For example, as described above, instances of a target sensor 108 may be provided to a number of different individuals or patients as part of a clinical trial, with the measurement outputs from the respective sensors 108 being uploaded or otherwise transmitted to a remote server 102 (e.g., via network 110) for storage in a database 104 in association with the respective individual or patient along with calibration data associated with the respective patient (e.g., timestamped reference blood glucose measurements and corresponding calibration factors) or other data associated with the respective patient (e.g., demographic data and/or the like).

In one embodiment, the generative modeling process 600 continues by associating measurement data with calibration data points (task 604). In this regard, measurement data 114 for the sensor 108 to be modeled is associated with concurrent or contemporaneous reference blood glucose measurement and related calibration data for a respective patient. For example, for each patient having a corresponding data set in the new sensor trial measurement data 114, the remote server 102 may identify different calibration data points associated with the patient, and then based on the associated timestamps (or sensor age or time after insertion), identify corresponding measurement outputs from the patient's sensor 108 that were obtained at the same time as or within a threshold amount of time of the respective calibration timestamp. In other words, the output measurements that are not temporally relevant to the calibration data points may be filtered or otherwise excluded from further analysis. Again, it should be noted that the measurement outputs from the patient's sensor 108 need not be synchronous with the respective calibration timestamp but may rather be within a threshold time of the calibration timestamp. Moreover, one or more values within the threshold time of the calibration timestamp may be averaged, interpolated, or otherwise combined to arrive at a representative value to be associated with the calibration timestamp.

After associating the measurement data with calibration data points, the generative modeling process 600 continues by developing or otherwise identifying a generative model for predicting the output measurements likely to be generated by the sensing arrangement as a function of the calibration factor and age (task 606). In exemplary embodiments, the generative model is implemented using a generative adversarial network made up of two neural networks. A first neural network is trained to derive a model, alternatively referred to herein as the generator model, using the respective pairs of calibration factors and timestamps (or sensor age) as conditional inputs to the generator model and the corresponding sets of sensor output measurements (e.g., electrical current, counter electrode voltage, electrochemical impedance, and the like) as the corresponding outputs to be produced by the generator model. In this regard, the generator model is capable of generating time-varying or time-dependent synthetic values for the sensor output measurements. A second neural network is trained using the same training data set to derive a model, alternatively referred to herein as the discriminator model, that votes or otherwise provides indication of whether a combination of input variables represents an actual or plausible combination of variables. Thus, for a given combination of sensor output measurement values (e.g., isig, Vctr and EIS values) and calibration data values (e.g., calibration factor and sensor age or time after insertion), the discriminator model provides an indication of whether that combination of input variables is plausible, such as, for example, a probability that the input variable combination is realistic. In exemplary embodiments, the generator and discriminator models are trained and function in concert with one another, such that the generator model generates values for the sensor output measurements for a given calibration factor and sensor age that maximizes or otherwise optimizes the output of the discriminator model.

After deriving a generative model, the generative modeling process 600 continues by retrieving or otherwise obtaining historical calibration data points and providing the historical calibration data points as input variables to the generative model to calculate or otherwise determine synthetic measurement data for the new sensor as a function of the historical calibration data points (tasks 608, 610). In this regard, the generative model may be applied to a set of historical calibration data that was previously obtained in connection with using an instance of the legacy sensor 106 to generate measurement outputs by the target sensor 108 that represent the probable electrochemical behavior of the target sensor 108 to the same stimulus and/or aging conditions that resulted in the input calibration factor at a particular sensor age. For example, if the database 104 maintains historical legacy sensor clinical trial measurement data 112 for 4000 different patients, the remote server 102 may retrieve the respective calibration data points (e.g., reference blood glucose measurement, calibration factor, and timestamp) for each individual patient, apply the generative model to each of the calibration data points for each individual patient to generate a synthetic measurement data set for that patient, and store the synthetic measurement data set associated with the target sensor 108 in the database 104, resulting in 4000 patient sets of simulated measurement data 118. In this manner, historical measurement data 112 from previous clinical trials may be utilized to effectively increase the amount of available clinical trial data for the new model, make, type, and/or configuration of sensing device 108 without requiring patients engage in such a trial. Synthetic data can also be created by the generative model by applying the generative model to simulated calibration data points.

In a similar manner as described above, after generating simulated measurement data for the particular type or configuration of sensing arrangement to be calibrated, the generative modeling process 600 continues by calculating or otherwise determining a glucose estimation model for predicting the patient's glucose level as a function of the measurement parameters output by the sensing arrangement using the simulated measurement data (task 612). For example, the remote server 102 may create an augmented set of measurement data for the target sensor 108 by combining the subset of observed target sensor clinical trial measurement data 114 associated with the calibration data points from the current clinical trial with the simulated measurement data 118 for the target sensor 108 associated with historical calibration data points to increase the size of the training data set for the glucose estimation model. In this regard, in a similar manner as described above, the glucose estimation model is trained using a training data set that includes the combinations of synthetic measurement outputs as input variables (e.g., generated isig, Vctr, and EIS values from the simulated measurement data 118) and the corresponding reference blood glucose measurement values from the historical data set (e.g., from historical legacy sensor data 112) as the output variable of the training data set.

In a similar manner as described above, the remote server 102 may analyze the observed new sensor trial measurement data 114 to derive the generative model and then store or otherwise maintain the data defining the generative model in the database 104 (e.g., modeling data 120) in association with the target sensor 108. Thereafter, the remote server 102 may apply the generative model to the calibration data points from the historical template sensor measurement data 112 from one or more previous trials to generate the simulated measurement data 118 corresponding to the historical calibration data points. The remote server 102 may then analyze the simulated measurement data 118, individually or in combination with the observed new sensor trial measurement data 114, to derive a glucose estimation model for the target sensor 108 using the synthetic measurement data. As described above, after determining the glucose estimation model for the target sensor 108, the remote server 102 may store or otherwise maintain the data defining the glucose estimation model in the database 104 (e.g., modeling data 120) in association with the target sensor 108 for distribution to other instances of the target sensor 108 or other electronic devices utilized with instances of the target sensor 108 (e.g., fluid infusion devices, client electronic devices, and/or the like).

In one embodiment, a generative modeling process involves obtaining measurement data from one sensor design, partitioning the measurement data into separate training, testing, and generative folds (an optional fold can be created for use in training the calibrated measurement algorithm), developing a generative model for sensor output based on features of sensor signals pre-conditioned on calibration data points from the training folds, and evaluating performance of the generative model by applying the generative model to extracted calibration data from the testing fold to evaluate performance. Then simulated data can be generated by applying the generative model to extracted calibration data from the generative folds or simulated and used to determine a predictive model for calibrated measurement output based on training with the simulated sensor measurements (synthetic data) generated sensor measurements with or without additional sensor measurements from the current sensor design.

Figure 7:
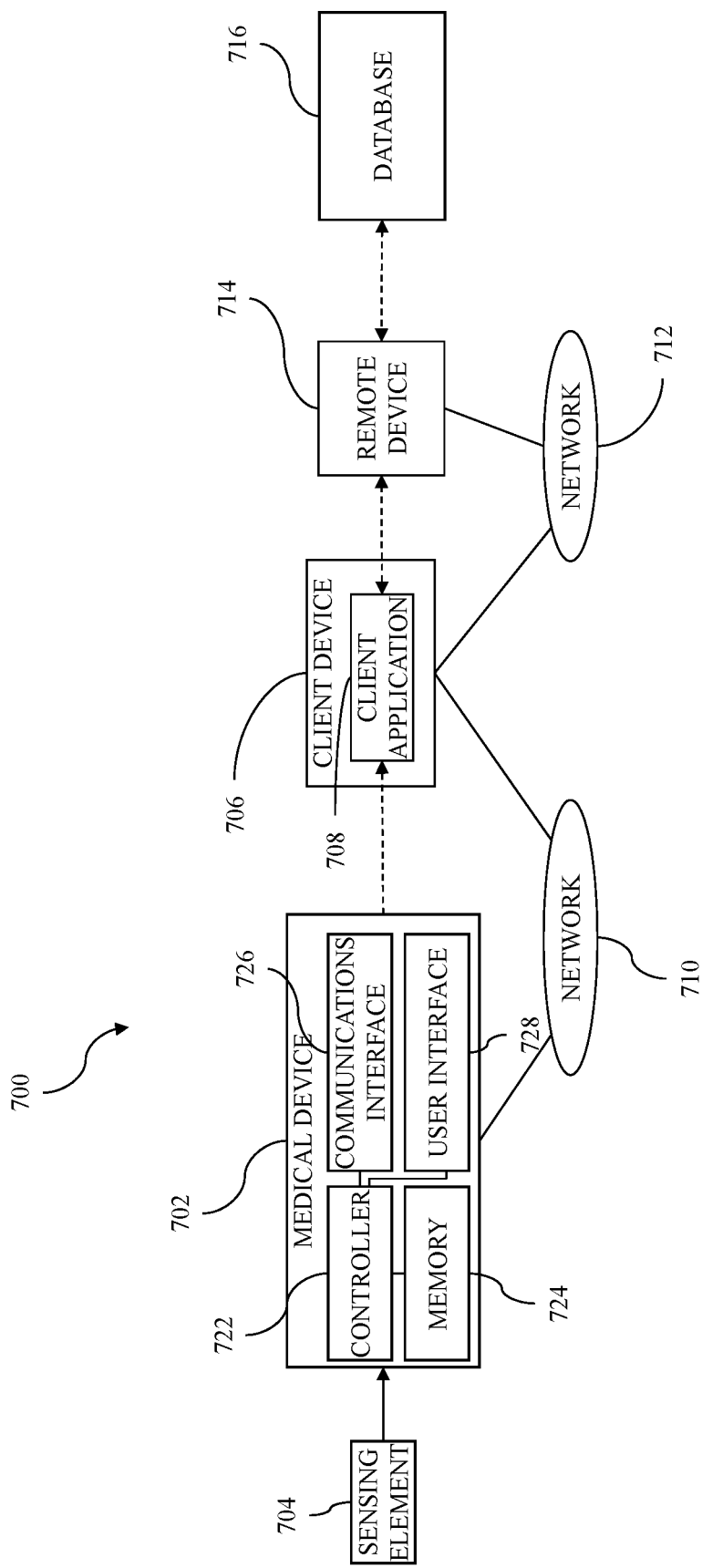
FIG. 7 depicts an exemplary embodiment of patient monitoring system suitable for use with one or more of the sensor translation process of FIG. 3, the real-time translation process of FIG. 5, and the generative modeling process of FIG. 6 in one or more exemplary embodiments.

FIG. 7 depicts an exemplary embodiment of a patient monitoring system 700 that includes a medical device 702 capable of using a glucose estimation model derived from simulated measurement data. In the illustrated embodiment, the medical device 702 is communicatively coupled to a sensing element 704 that is inserted into the body of a patient or otherwise worn by the patient to obtain measurement data indicative of a physiological condition in the body of the patient, such as a sensed glucose level. In the illustrated embodiment, the medical device 702 is communicatively coupled to a client device 706 via a communications network 710, with the client device 706 being communicatively coupled to a remote device 714 (e.g., remote server 102) via another communications network 712 (e.g., network 110). In this regard, the client device 706 may function as an intermediary for uploading or otherwise providing measurement data from the medical device 702 to the remote device 714. It should be appreciated that FIG. 7 depicts a simplified representation of a patient monitoring system 700 for purposes of explanation and is not intended to limit the subject matter described herein in any way. For example, some embodiments may support direct communications between the medical device 702 and the remote device 714 via communications network 712.

In exemplary embodiments, the client device 706 is realized as a mobile phone, a smartphone, a tablet computer, or other similar mobile electronic device; however, in other embodiments, the client device 706 may be realized as any sort of electronic device capable of communicating with the medical device 702 via network 710, such as a laptop or notebook computer, a desktop computer, or the like. In exemplary embodiments, the network 710 is realized as a Bluetooth network, a ZigBee network, or another suitable personal area network. That said, in other embodiments, the network 710 could be realized as a wireless ad hoc network, a wireless local area network (WLAN), or local area network (LAN). The client device 706 includes or is coupled to a display device, such as a monitor, screen, or another conventional electronic display, capable of graphically presenting data and/or information pertaining to the physiological condition of the patient. The client device 706 also includes or is otherwise associated with a user input device, such as a keyboard, a mouse, a touchscreen, or the like, capable of receiving input data and/or other information from the user of the client device 706.

In some embodiments, a user, such as the patient, the patient's doctor or another healthcare provider, or the like, manipulates the client device 706 to execute a client application 708 that supports communicating with the medical device 702 via the network 710. In this regard, the client application 708 supports establishing a communications session with the medical device 702 on the network 710 and receiving data and/or information from the medical device 702 via the communications session. The medical device 702 may similarly execute or otherwise implement a corresponding application or process that supports establishing the communications session with the client application 708. The client application 708 generally represents a software module or another feature that is generated or otherwise implemented by the client device 706 to support the processes described herein. Accordingly, the client device 706 generally includes a processing system and a data storage element (or memory) capable of storing programming instructions for execution by the processing system, that, when read and executed, cause processing system to create, generate, or otherwise facilitate the client application 708 and perform or otherwise support the processes, tasks, operations, and/or functions described herein. Depending on the embodiment, the processing system may be implemented using any suitable processing system and/or device, such as, for example, one or more processors, central processing units (CPUs), graphics processing units (GPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 706 and the medical device 702 establish an association (or pairing) with one another over the network 710 to support subsequently establishing a point-to-point communications session between the medical device 702 and the client device 706 via the network 710. For example, in accordance with one embodiment, the network 710 is realized as a Bluetooth network, wherein the medical device 702 and the client device 706 are paired with one another (e.g., by obtaining and storing network identification information for one another) by performing a discovery procedure or another suitable pairing procedure. The pairing information obtained during the discovery procedure allows either of the medical device 702 or the client device 706 to initiate the establishment of a secure communications session via the network 710.

In one or more exemplary embodiments, the client application 708 is also configured to store or otherwise maintain a network address and/or other identification information for the remote device 714 on the second network 712. In this regard, the second network 712 may be physically and/or logically distinct from the network 710, such as, for example, the Internet, a cellular network, a wide area network (WAN), or the like. The remote device 714 generally represents a server or other computing device configured to receive and analyze or otherwise monitor measurement data, event log data, and potentially other information obtained for the patient associated with the medical device 702. In exemplary embodiments, the remote device 714 is coupled to a database 716 (e.g., database 104) configured to store or otherwise maintain data associated with individual patients. In practice, the remote device 714 may reside at a location that is physically distinct and/or separate from the medical device 702 and the client device 706, such as, for example, at a facility that is owned and/or operated by or otherwise affiliated with a manufacturer of the medical device 702. For purposes of explanation, but without limitation, the remote device 714 may alternatively be referred to herein as a server.

It should be noted that in some embodiments, some or all of the functionality and processing intelligence of the remote computing device 714 can reside at the medical device 702 and/or at other components or computing devices that are compatible with the patient monitoring system 700. In other words, the patient monitoring system 700 need not rely on a network-based or a cloud-based server arrangement as depicted in FIG. 7, although such a deployment might be the most efficient and economical implementation. These and other alternative arrangements are contemplated by this disclosure. To this end, some embodiments of the system 700 may include additional devices and components that serve as data sources, data processing units, and/or recommendation delivery mechanisms. For example, the system 700 may include any or all of the following elements, without limitation: computer devices or systems; patient monitors; healthcare provider systems; data communication devices; and the like.

Still referring to FIG. 7, the sensing element 704 generally represents the component of the patient monitoring system 700 that is configured to generate, produce, or otherwise output one or more electrical signals indicative of a physiological condition that is sensed, measured, or otherwise quantified by the sensing element 704 (e.g., sensing element 202). In this regard, the physiological condition of a patient influences a characteristic of the electrical signal output by the sensing element 704, such that the characteristic of the output signal corresponds to or is otherwise correlative to the physiological condition that the sensing element 704 is sensitive to. In exemplary embodiments, the sensing element 704 is realized as an interstitial glucose sensing element inserted at a location on the body of the patient that generates an output electrical signal having a current (or voltage) associated therewith that is correlative to or otherwise influenced by the interstitial fluid glucose level that is sensed or otherwise measured in the body of the patient by the sensing element 704. In some embodiments, the sensing element 704 is implemented or otherwise realized as an instance of the target sensing device 108, 200 (or new sensor) having an associated glucose estimation model derived using simulated measurement data.

The medical device 702 generally represents the component of the patient monitoring system 700 that is communicatively coupled to the output of the sensing element 704 to receive or otherwise obtain the measurement data samples from the sensing element 704 (e.g., the measured glucose and characteristic impedance values), store or otherwise maintain the measurement data samples, and upload or otherwise transmit the measurement data to the server 714 via the client device 706. In one or more embodiments, the medical device 702 is realized as an infusion device configured to deliver a fluid, such as insulin, to the body of the patient. In such embodiments, the infusion device 702 may employ closed-loop control or other delivery control schemes that vary insulin delivery in a manner that is influenced by the patient's current glucose level received via the sensing element 704 or other sensing device (e.g., a continuous glucose monitor (CGM) device). That said, in other embodiments, the medical device 702 could be a standalone sensing or monitoring device separate and independent from an infusion device (e.g., sensing device 108, 200), such as, for example, a continuous glucose monitor (CGM) (or CGM device), an interstitial glucose sensing arrangement, or similar device. It should be noted that although FIG. 7 depicts the medical device 702 and the sensing element 704 as separate components, in practice, the medical device 702 and the sensing element 704 may be integrated or otherwise combined to provide a unitary device that can be worn by the patient.

In exemplary embodiments, the medical device 702 includes a controller 722, a data storage element 724 (or memory), a communications interface 726, and a user interface 728. The user interface 728 generally represents the input user interface element(s) and/or output user interface element(s) associated with the medical device 702. The controller 722 generally represents the processing system or other hardware, circuitry, logic, firmware and/or other component(s) of the medical device 702 that is coupled to the sensing element 704 to receive the electrical signals output by the sensing element 704 and perform or otherwise support various additional tasks, operations, functions and/or processes described herein. Depending on the embodiment, the controller 722 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the controller 722 includes an analog-to-digital converter (ADC) or another similar sampling arrangement that samples or otherwise converts an output electrical signal received from the sensing element 704 into corresponding digital measurement data value. In other embodiments, the sensing element 704 may incorporate an ADC and output a digital measurement value.

The communications interface 726 generally represents the hardware, circuitry, logic, firmware and/or other components of the medical device 702 that are coupled to the controller 722 for outputting data and/or information from/to the medical device 702 to/from the client device 706. For example, the communications interface 726 may include or otherwise be coupled to one or more transceiver modules capable of supporting wireless communications between the medical device 702 and the client device 706. In exemplary embodiments, the communications interface 726 is realized as a Bluetooth transceiver or adapter configured to support Bluetooth Low Energy (BLE) communications.

In exemplary embodiments, the remote device 714 receives, from the client device 706, measurement data values associated with a particular patient (e.g., sensor glucose measurements, acceleration measurements, and the like) that were obtained using the sensing element 704, and the remote device 714 stores or otherwise maintains the historical measurement data in the database 716 in association with the patient (e.g., using one or more unique patient identifiers). Additionally, the remote device 714 may also receive, from or via the client device 706, meal data or other event log data that may be input or otherwise provided by the patient (e.g., via client application 708) and store or otherwise maintain historical meal data and other historical event or activity data associated with the patient in the database 716. In this regard, the meal data include, for example, a time or timestamp associated with a particular meal event, a meal type or other information indicative of the content or nutritional characteristics of the meal, and an indication of the size associated with the meal. In exemplary embodiments, the remote device 714 also receives historical fluid delivery data corresponding to basal or bolus dosages of fluid delivered to the patient by an infusion device. For example, the client application 708 may communicate with an infusion device to obtain insulin delivery dosage amounts and corresponding timestamps from the infusion device, and then upload the insulin delivery data to the remote device 714 for storage in association with the particular patient. The remote device 714 may also receive geolocation data and potentially other contextual data associated with a device 702, 706 from the client device 706 and/or client application 708, and store or otherwise maintain the historical operational context data in association with the particular patient. In this regard, one or more of the devices 702, 706 may include a global positioning system (GPS) receiver or similar modules, components or circuitry capable of outputting or otherwise providing data characterizing the geographic location of the respective device 702, 706 in real-time.

In various embodiments, the remote device 714 may implement, facilitate, support or otherwise perform the sensor translation process 300 of FIG. 3 or the generative modeling process 600 of FIG. 6 to obtain a glucose estimation model associated with the sensing element 704. Thereafter, the remote device 714 may push or otherwise provide the glucose estimation model to the medical device 702 and/or the client device 706 for determining an estimated sensor glucose value in real-time based on measurement data samples obtained via sensing arrangement 704. For example, when the medical device 702 is realized as an infusion device, the glucose estimation model may be utilized to adjust or otherwise augment the current sensor glucose measurement value determined using a calibration factor with a current estimated sensor glucose value to arrive at an adjusted sensor glucose measurement value that accounts for aging of the sensing element 704 since the most recent calibration. Based on a difference between the adjusted sensor glucose measurement value and a target glucose value for a patient, the infusion device 702 may determine a corresponding amount of insulin to be delivered to reduce the different and autonomously operate a motor or other actuation arrangement of the infusion device 702 in accordance with the delivery command to displace a plunger or otherwise dispense insulin from a reservoir of the infusion device 702. That said, in other embodiments, the medical device 702 and/or the client application 708 may utilize the current estimated sensor glucose value and/or the adjusted sensor glucose measurement value to provide alerts or other notifications to a user (e.g., hyperglycemia and/or hypoglycemia alerts, alerts to replace or change the sensing element 704, alerts to change the insertion site for the sensing element 704, etc.). In this regard, the subject matter described herein is not limited to any particular application or use of the glucose estimation model or estimated sensor glucose values determined therefrom. Additionally, as described, in various embodiments, the remote device 714 may facilitate or otherwise support development of different sensor translation models, generative models, and the like in connection with one or more of the processes 300, 500, 600 described above using measurement data maintained in the database 716, maintain the modeling data (e.g., in the database 716), and push or otherwise provide modeling data to different instances of the medical device 702 (e.g., sensors 106, 108) as appropriate for real-time deployment or application at a medical device 702.

In one or more embodiments, the remote device 714 may facilitate or otherwise support the real-time translation process 500 of FIG. 5 by developing and providing a translation model to the medical device 702 and/or the client device 706 for translating measurement data samples obtained via the sensing arrangement 704 to a legacy sensor domain in real-time. For example, the medical device 702 may utilizes the translation model to translate measurements captured via the sensing element 202, 704 of a new sensor design or configuration into simulated measurements in a legacy sensor domain, and then apply a legacy glucose estimation model to the simulated measurements to obtain an estimated calibrated measurement value that may be utilized by the medical device 702 (e.g., to determine insulin delivery commands, generate graphical user interface displays, and/or the like) or provided to another device 706. Thus, a sensing element 704 with a new design or configuration could be deployed in the system 700 without a new calibration algorithm (or glucose estimation model) being trained or developed for the sensing element 704, but rather, estimated or predicted calibrated measurement outputs may be obtained in accordance with an existing calibration algorithm, thereby allowing well performing algorithms established for other sensors to be deployed in connection with sensing element 704.

For the sake of brevity, conventional techniques related to glucose sensing and/or monitoring, sampling, filtering, calibration, closed-loop glucose control, machine learning, artificial intelligence, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of estimating a physiological condition using data associated with different sensing arrangements, the method comprising:
   obtaining, by a processing system, a sensor translation model associated with a relationship between a first sensing arrangement and a second sensing arrangement, wherein:
     the first sensing arrangement comprises a first sensing element configured to measure the physiological condition,
     the second sensing arrangement comprises a second sensing element configured to measure the same physiological condition, and
     the sensor translation model is based on measurements from the first sensing element and corresponding measurements from the second sensing element;
   obtaining, by the processing system, one or more measurements from the first sensing element in a first instance of the first sensing arrangement;
   determining, by the processing system, simulated measurement data for the second sensing arrangement by applying the sensor translation model to the one or more measurements from the first sensing element in the first instance of the first sensing arrangement, wherein the simulated measurement data represents one or more measurements that the second sensing element of the second sensing arrangement would output in response to a value of the physiological condition that resulted in the one or more measurements from the first sensing element in the first instance of the first sensing arrangement; and determining, by the processing system, an estimated value of the physiological condition by applying an estimation model associated with the second sensing arrangement to the simulated measurement data, wherein the estimation model is different from the sensor translation model.

2. The method of claim 1, wherein obtaining the sensor translation model comprises:

obtaining first measurement data from different instances of the first sensing arrangement;

obtaining second measurement data from different instances of the second sensing arrangement concurrent to the first measurement data; and determining the sensor translation model based on relationships between the first measurement data and the second measurement data.

3. The method of claim 2, wherein determining the sensor translation model comprises training the sensor translation model using the first measurement data and the second measurement data as inputs to the sensor translation model.

4. The method of claim 2, wherein determining the sensor translation model comprises determining the sensor translation model based on relationships between the first measurement data and the second measurement data, using a series of invertible, memory-less transforms to shift sensing signals between a first domain associated with the first sensing arrangement and a second domain associated with the second sensing arrangement.

5. The method of claim 2, wherein determining the sensor translation model comprises determining the sensor translation model based on relationships between the first measurement data and the second measurement data using a concatenative modeling technique.

6. The method of claim 1, further comprising downloading, by the processing system, the estimation model associated with the second sensing arrangement from a remote server via a network.

7. The method of claim 6, wherein obtaining the sensor translation model comprises downloading, by the processing system, the sensor translation model from the remote server via the network.

8. The method of claim 1, further comprising outputting, by the processing system, the estimated value of the physiological condition.

9. The method of claim 1, wherein the first sensing arrangement comprises a new sensing arrangement influenced by the physiological condition and the second sensing arrangement comprises a legacy sensing arrangement influenced by the physiological condition.

10. The method of claim 9, wherein:
the physiological condition comprises a glucose level;
the new sensing arrangement comprises a new glucose sensor;
the legacy sensing arrangement comprises a legacy glucose sensor; and
the estimation model comprises a sensor glucose estimation model associated with the legacy glucose sensor.

11. The method of claim 1, wherein the first sensing arrangement comprises a template sensing device influenced by the physiological condition and the second sensing arrangement comprises a target sensing device influenced by the physiological condition, and wherein the method further comprises:

obtaining first measurement data from different instances of the template sensing device;

obtaining second measurement data from different instances of the target sensing device concurrent to the first measurement data, wherein respective sets of the first measurement data and the second measurement data are concurrently obtained from a respective common patient using respective instances of the template sensing device and the target sensing device; and determining the sensor translation model based at least in part on relationships between the first measurement data and the second measurement data.

12. The method of claim 11, further comprising:

obtaining reference values for the physiological condition together with third measurement data associated with the reference values, wherein the third measurement data comprises historical measurements from additional instances of the target sensing device; and training the estimation model using the third measurement data as an input to the estimation model and the reference values as an output of the estimation model.

13. The method of claim 11, wherein determining the sensor translation model comprises training the sensor translation model using the first measurement data as an input to the sensor translation model and using the second measurement data as an output of the sensor translation model.

14. The method of claim 11, wherein determining the sensor translation model comprises determining the sensor translation model based on relationships between the first measurement data and the second measurement data, using a series of invertible, memory-less transforms to shift sensing signals from a first domain associated with the first sensing arrangement to a second domain associated with the second sensing arrangement.

15. The method of claim 11, wherein determining the sensor translation model comprises determining the sensor translation model based on relationships between the first measurement data and the second measurement data using a concatenative modeling technique.

16. The method of claim 1, wherein the first sensing arrangement comprises a legacy sensing arrangement influenced by the physiological condition and the second sensing arrangement comprises a new sensing arrangement influenced by the physiological condition.

17. The method of claim 16, wherein:
the physiological condition comprises a glucose level;
the new sensing arrangement comprises a new glucose sensor;
the legacy sensing arrangement comprises a legacy glucose sensor; and
the estimation model comprises a sensor glucose estimation model associated with the new glucose sensor.

18. The method of claim 1, further comprising determining a delivery command for operating an actuation arrangement of an infusion device based at least in part on the estimated value of the physiological condition.

19. The method of claim 1, wherein the one or more measurements from the first sensing element in the first instance of the first sensing arrangement comprise at least one: current values, voltage values, or electrochemical impedance values, and wherein the simulated measurement data for the second sensing arrangement comprises at least one of: current values, voltage values, or electrochemical impedance values.

20. The method of claim 1, wherein the estimation model has been pre-trained using measurements from one or more instances of the second sensing arrangement.

21. The method of claim 1, wherein:
the first sensing element and the second sensing element are glucose sensing elements,
the one or more measurements from the first sensing element in the first instance of the first sensing arrangement comprise a value of a signal produced by the first sensing element in response to a particular glucose level, and
the simulated measurement data comprises a value of a signal that the second sensing element would output in response to the particular glucose level.

* * * * *